United States Patent [19]

Bolin

[11] Patent Number: 5,141,924
[45] Date of Patent: Aug. 25, 1992

[54] SYNTHETIC VASOACTIVE INTESTINAL PEPTIDE ANALOGS

[75] Inventor: David R. Bolin, Denville, N.J.

[73] Assignee: Hoffmann-La Roche, Inc., Nutley, N.J.

[21] Appl. No.: 374,503

[22] Filed: Jun. 30, 1989

[51] Int. Cl.$^5$ ............... A61K 37/02; C07K 7/10
[52] U.S. Cl. ............................ 514/12; 514/20; 530/324; 530/325; 930/170; 930/DIG. 821; 930/DIG. 820; 930/DIG. 800
[58] Field of Search ........... 530/324, 325; 514/12, 514/20; 930/170, DIG. 821, DIG. 820, DIG. 800

[56] References Cited

U.S. PATENT DOCUMENTS

| | | | |
|---|---|---|---|
| 4,605,641 | 8/1986 | Bolin et al. | 514/12 |
| 4,734,400 | 3/1988 | Bolin et al. | 514/12 |
| 4,737,487 | 4/1988 | Watts et al. | 514/15 |
| 4,822,774 | 4/1989 | Ito et al. | 514/12 |
| 4,835,252 | 5/1989 | Musso et al. | 530/324 |

FOREIGN PATENT DOCUMENTS

| | | | |
|---|---|---|---|
| 0297068 | 12/1968 | European Pat. Off. | 514/12 |
| 0184309 | 6/1986 | European Pat. Off. | |
| 8806598 | 9/1988 | PCT Int'l Appl. | |
| 8905857 | 6/1989 | World Int. Prop. O. | |

OTHER PUBLICATIONS

Biochemical & Biophysical Research Comm. vol. 121, No. 2, 1984, pp. 493-498.
Peptides, Chemistry & Biology, Marshall, pp. 440-443, 1988.
Schaaper et al., Chem. Abs. vol. 100, No. 19, 156971m, (1984) [Recl., J.R. Neth. Chem. Soc. 103(1) pp. 17-22].
Musso et al., Biochemistry, vol. 27, pp. 8174-8181, (1988).
Barnes, Pharmac. Ther., vol. 36, pp. 119-129 (1988).
Pandol et al., "VIP Receptor Antagonist", Rapid Communication, G553-G557, (1986).
Tachibana et al., Peptide Chemistry, pp. 481-486, (1987).

Primary Examiner—Merrell C. Cashion, Jr.
Assistant Examiner—T. D. Wessendorf
Attorney, Agent, or Firm—George M. Gould; William H. Epstein; Bruce A. Pokras

[57] ABSTRACT

Vasoactive intestinal peptide analogs containing substitutions of appropriately selected amino acids at specific positions of the VIP molecule.

16 Claims, No Drawings

SYNTHETIC VASOACTIVE INTESTINAL PEPTIDE ANALOGS

BACKGROUND OF THE INVENTION

Vasoactive intestinal peptide (VIP) was first discovered, isolated and purified from porcine intestine. [U.S. Pat. No. 3,879,371]. The peptide has twenty-eight (28) amino acids and bears extensive homology to secretin and glucagon. [Carlquist et al., Horm. Metab. Res., 14, 28–29 (1982)]. The amino acid sequence of VIP is as follows:

His—Ser—Asp—Ala—Val—Phe—Thr—Asp—Asn—Tyr—Thr—Arg—Leu—Arg—Lys—Gln—Met—Ala—Val—Lys—Lys—Tyr—Leu—Asn—Ser—Ile—Leu—Asn—NH$_2$

VIP is known to exhibit a wide range of biological activities throughout the gastrointestinal tract and circulatory system. In light of its similarity to gastrointestinal hormones, VIP has been found to stimulate pancreatic and biliary secretion, hepatic glycogenolysis, glucagon and insulin secretion and to activate pancreatic bicarbonate release. [Kerrins, C. and Said, S. I., Proc. Soc. Exp. Biol. Med., 142, 1014–1017 (1972), Domschke, S. et al., Gastroenterology, 73, 478–480 (1977)].

Neurons containing VIP have been localized by immunoassay in cells of the endocrine and exocrine systems, intestine and smooth muscle. [Polak, J. M. et al., Gut, 15, 720–724 (1974)]. VIP has been found to be a neuroeffector causing the release of several hormones including prolactin [Frawley, L. S., et al., Neuroendocrinology, 33, 79–83 (1981)], thyroxine [Ahren, B., et al., Nature, 287, 343–345 (1980)], and insulin and glucagon [Schebalin, M., et al., Am. J. Physiology E., 232, 197–200 (1977)]. VIP has also been found to stimulate renin release from the kidney in vivo and in vitro. [Porter, J. P., et al. Neuroendocrinology, 36, 404–408 (1983)]. VIP has been found to be present in nerves and nerve terminals in the airways of various animal species and man. [Dey, R. D., and Said, S. I., Fed. Proc., 39, 1062 (1980), Said, S. I., et al., Ann. N.Y. Acad. Sciences, 221, 103–114 (1974)]. VIP's cardiovascular and bronchopulmonary effects are of interest as VIP has been found to be a powerful vasodilator and potent smooth muscle relaxant, acting on peripheral, pulmonary, and coronary vascular beds. [Said, S. I., et al., Clin. Res., 20, 29 (1972)]. VIP has been found to have a vasodilatory effect on cerebral blood vessels. [Lee, T. J. and Berszin, I., Science, 224, 898–900 (1984)]. In vitro studies demonstrated that vasoactive intestinal peptide, applied exogenously to cerebral arteries induced vasodilation, suggesting VIP as a possible transmitter for cerebral vasodilation. [Lee, T. and Saito, A., Science, 224, 898–901 (1984)]. In the eye, VIP has also been shown to be a potent vasodilator [Nilsson, S. F. E. and Bill, A., Acta Physiol. Scand., 121, 385–392 (1984)].

VIP may have regulatory effects on the immune system. O'Dorisio et al have shown that VIP can modulate the proliferation and migration of lymphocytes. [J. Immunol., 135, 792s–796s (1985)].

Since VIP has been found to relax smooth muscle and it is normally present in airway tissues, it has been hypothesized that VIP may be an endogenous mediator of bronchial smooth muscle relaxation. [Dey, R. D. and Said, S. I., Fed. Proc., 39, 1062 (1980)]. In vitro and in vivo testing have shown VIP to relax tracheal smooth muscle and protect against bronchoconstrictor agents such as histamine and prostaglandin F$_{2a}$. [Wasserman, M. A. et al., in Vasoactive Intestinal Peptide, S. I. Said, ed., Raven Press, N.Y., 1982, pp 177–184. Said, S. I. et al., Ann. N.Y. Acad. Sci., 221, 103–114 (1974)]. When giving intravenously, VIP has been found to protect against bronchoconstrictor agents such as histamine, prostaglandin F$_{2a}$, leukotrienes, platelet activating factor as well as antigen-induced bronchoconstrictions. [Said, S. I., et al., supra, (1982)]. VIP has also been found to inhibit mucus secretion in human airway tissue in vitro. [Coles, S. J. et al., Am. Rev. Respir. Dis., 124, 531–536 (1981)].

In man, when administered by intravenous infusion to asthmatic patients, VIP has been shown to cause an increase in peak expiratory flow rate and protect against histamine-induced bronchodilation. [Morice, A. H. and Sever, P. S., Peptides, 7, 279–280 (1986); Morice, A. et al., The Lancet, II 1225–1227 (1983)]. The pulmonary effects observed by this intravenous infusion of VIP were, however, accompanied by cardiovascular side-effects, most notably hypotension and tachycardia and also facial flushing. When given in intravenous doses which did not cause cardiovascular effects, VIP failed to alter specific airway conductance. [Palmer et al., Thorax, 41, 663–666 (1986)]. The lack of activity was explained as being due to the low dose administered and possibly due to rapid degradation of the compound.

When administered by aerosol to humans, native VIP has been only marginally effective in protecting against histamine-induced bronchoconstriction [Altieri et al., Pharmacologist, 25, 123 (1983)]. VIP was found to have no significant effect on baseline airway parameters but did have a protective effect against histamine-induced bronchoconstriction when given by inhalation to humans. [Barnes, P. J. and Dixon, C. M. S., Am. Rev. Respir. Dis., 130, 162–166 (1984)]. VIP when given by aerosol has been reported to display no tachycardia or hypotensive effects in conjunction with the bronchodilation. [Said, S. I. et al., in Vasoactive Intestinal Peptide, S. I. Said, ed., Raven Press, N.Y., 1928, pp 185–191].

Because of the interesting and potential clinically useful biological activities of VIP, this substance has been the target of several reported synthetic programs with the goal of enhancing one or more of the properties of this molecule. Takeyama et al. have reported a VIP analog having a glutamic acid substituted for aspartic acid at position 8. This compound was found to be less potent than native VIP. [Chem. Pharm. Bull., 28, 2265–2269 (1980)]. Wendlberger et al. have disclosed the preparation of a VIP analog having norleucine substituted at position 17 for methionine. [Peptide, Proc. 16th Eur. Pept. Symp., 290–295 (1980)]. The peptide was found to be equipotent to native VIP for its ability to displace radioiodinated VIP from liver membrane preparations. Turner et al. have reported that the fragment VIP(10-28) is an antagonist to VIP. [Peptides, 7, 849–854 (1986)]. The substituted analog [4-Cl-D-Phe$^6$,-Leu$^{17}$]-VIP has also been reported to bind to the VIP receptor and antagonize the activity of VIP. [Pandol, S. et al., Gastrointest. Liver Physiol., 13, G553–G557 (1986)]. P. Robberecht et al. have reported several VIP analogs with D-residues substituted in the N-terminus of native VIP. [Peptides, 9, 339–345 (1988)]. All of these analogs bound less tightly to the VIP receptor and showed lower activity than native VIP in c-AMP activation. S. Tachibana and O. Ito have reported several VIP analogs of the precursor molecule. [in Peptide Chem., T. Shiba and S. Sakakibara, eds., Prot. Res. Foundation, 1988, pp. 481-486]. These compounds were shown to be 1 to 3 fold more potent bronchodilators than VIP and had 1 to 2 fold more hypotensive activity. Musso et al. have also reported several VIP analogs with substitutions at positions 6-7, 9-13, 15-17, and 19-28. [Biochemistry, 27, 8174-8181 (1988); Eur. Pat. 88271141]. These compounds were found to be equal to or less potent than native VIP in binding to the VIP receptor and in biological response.

SUMMARY OF THE INVENTION

The instant invention comprises compounds of the formula:

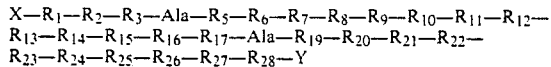

wherein $R_1$ is His, Ala, N-CH$_3$-Ala, D-Ala, Gly, pyro-Glu, B-Ala or deleted; $R_2$ is Ser or Ala; $R_3$ is Asp or Ala; $R_5$ is Val, Leu or Ala; $R_6$ is Trp, Ala or

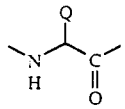

where Q =

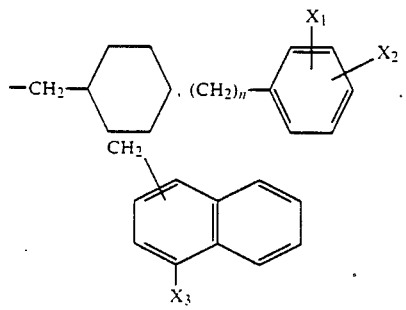

n = 1,2; $X_1$ and $X_2$ are each independently H, OH, OCH$_3$, F, Cl, I, CH$_3$, CF$_3$, NO$_2$, NH$_2$, N(CH$_3$)$_2$, NHCOCH$_3$, NHCOC$_6$H$_5$, or C(CH$_3$)$_3$; $X_3$ is H or F; $R_7$ is Thr or Ala; $R_8$ is Asp, Glu or Ala; $R_9$ is Asn or Ala; $R_{10}$ is Tyr, Trp, Ala, or $R_6$; $R_{11}$ is Thr or Ala; $R_{12}$ is Arg, Lys, Orn or Ala; $R_{13}$ is Leu or Ala; $R_{14}$ is Arg, Lys or Ala; $R_{15}$ is Lys or Ala; $R_{16}$ is Gln or Ala; $R_{17}$ is Met, Nle or Ala; $R_{19}$ is Val or Ala; $R_{20}$ is Lys or Ala; $R_{21}$ is Lys or Ala; $R_{22}$ is Tyr, Trp, Ala or $R_6$; $R_{23}$ is Leu or Ala; $R_{24}$ is Asn or Ala; $R_{25}$ is Ser, Thr or Ala; $R_{26}$ is Ile, Val, Leu or Ala; $R_{27}$ is Leu, Lys or Ala; $R_{28}$ is Asn, Thr, Lys or Ala; X is hydrogen,

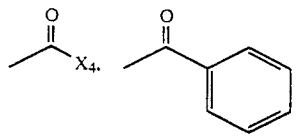

$X_4$ is C$_{1-3}$ alkyl or halo(C$_{1-3}$)alkyl, CH$_3$SO$_2$—, CH$_3$NHCO—, CH$_3$OCO—, or CH$_3$S(O)$_n$(CH$_2$)$_2$CO—, where n = 0-2; Y is —OX$_5$, —NHX$_5$ or R$_{29}$-R$_{30}$-R$_{31}$-Z; X$_5$ is H or C$_{1-3}$ alkyl; R$_{29}$ is Gly or Ala; R$_{30}$ is Gly, Lys or Ala; R$_{31}$ is Gly, Ala, Met, Cys, Cys(Acm), Thr, Ser, Phe or —NHX$_5$; Z is —OX$_5$ or —NHX$_5$; and the pharmaceutically acceptable acid or base addition salts thereof.

DETAILED DESCRIPTION OF THE INVENTION

As used herein, the term "C$_{1-3}$ alkyl" refers to methyl, ethyl, propyl, and isopropyl.

The nomenclature used to define the peptides is that typically used in the art wherein the amino group at the N-terminus appears to the left and the carboxyl group at the C-terminus appears to the right. By natural amino acids is meant one of the naturally occuring amino acids found in proteins, i.e., Gly, Ala, Val, Leu, Ile, Ser, Thr, Lys, Arg, Asp, Asn, Glu, Gln, Cys, Met, Phe, Tyr, Pro, Trp, and His. By Nle is meant norleucine. By Orn is meant ornithine. By Ac is meant acetyl (CH$_3$CO—). Where the amino acid has isomeric forms, it is the L form of the amino acid that is represented unless otherwise expressly indicated.

Analogs of VIP are indicated by setting forth the substituted amino acid in brackets before "VIP". Derivatization of the N-terminal amino group, i.e. as by X above, is indicated to the left of the bracketed substitutions. Sequence numbers appearing in parentheses to the right of "VIP" indicate amino acid deletions and additions to the native sequence numbering. That is, for example, Ac-[Lys$^{12}$,Nle$^{17}$,Gly$^{29}$]-VIP(2-29) indicates a polypeptide having an amino acid sequence corresponding to native human VIP in which an acetyl group has been substituted for hydrogen at the N-terminus, a lysine has been substituted for arginine at position 12 and a norleucine has been substituted for methionine at position 17. Additionally, the histidine at position 1 has been deleted and a glycine has been coupled onto the carboxyl side of asparagine 28, termed position 29. The suffixes "—OH" and "—NH$_2$" following VIP refer to the free acid and amide forms of the polypeptide, respectively. In the event neither suffix is used, the expression is intended to encompass both forms.

The following abbreviations are also defined:
N-CH$_3$-Ala is N-methyl-alanine
p-F-Phe is Fluoro-phenylalanine
1-Nal is 3-(1'-naphthyl)-alanine
2-Nal is 3-(2'-naphthyl)-alanine
p-NH$_2$-Phe is p-amino-phenylalanine
O-CH$_3$-Tyr is O-methyl-tyrosine
Cys(Acm) is S-acetoamidomethyl-cysteine
m-F-Tyr is m-Fluoro-tyrosine Representative compounds of the present invention include peptides having the following amino acid sequences:
Ac-[Lys$^{12}$,Nle$^{17}$,Val$^{26}$,Ala$^{28}$]-VIP
Ac-[Lys$^{12}$,Nle$^{17}$,Val$^{26}$,Ala$^{27}$,Thr$^{28}$]-VIP
Ac-[Lys$^{12}$,Nle$^{17}$,Ala$^{26}$,Thr$^{28}$]-VIP
Ac-[Lys$^{12}$,Nle$^{17}$,Ala$^{25}$,Val$^{26}$,Thr$^{28}$]-VIP
Ac-[Lys$^{12}$,Nle$^{17}$,Ala$^{24}$,Val$^{26}$,Thr$^{28}$]-VIP
Ac-[Lys$^{12}$,Nle$^{17}$,Ala$^{23}$,Val$^{26}$,Thr$^{28}$]-VIP
Ac-[Lys$^{12}$,Nle$^{17}$,Ala$^{22}$,Val$^{26}$,Thr$^{28}$]-VIP
Ac-[Lys$^{12}$,Nle$^{17}$,Ala$^{21}$,Val$^{26}$,Thr$^{28}$]-VIP
Ac-[Lys$^{12}$,Nle$^{17}$,Ala$^{20}$,Val$^{26}$,Thr$^{28}$]-VIP
Ac-[Lys$^{12}$,Nle$^{17}$,Ala$^{19}$,Val$^{26}$,Thr$^{28}$]-VIP
Ac-[Lys$^{12}$,Ala$^{17}$,Val$^{26}$,Thr$^{28}$]-VIP
Ac-[Lys$^{12}$,Ala$^{16}$,Nle$^{17}$,Val$^{26}$,Thr$^{28}$]-VIP
Ac-[Lys$^{12}$,Ala$^{15}$,Nle$^{17}$,Val$^{26}$,Thr$^{28}$]-VIP
Ac-[Lys$^{12}$,Ala$^{14}$,Nle$^{17}$,Val$^{26}$,Thr$^{28}$]-VIP
Ac-[Lys$^{12}$,Ala$^{13}$,Nle$^{17}$,Val$^{26}$,Thr$^{28}$]-VIP Ac-[Ala$^{12}$,Nle$^{17}$,Val$^{26}$,Thr$^{28}$]-VIP
Ac-[Ala$^{11}$,Lys$^{12}$,Nle$^{17}$,Val$^{26}$,Thr$^{28}$]-VIP
Ac-[Ala$^{10}$,Lys$^{12}$,Nle$^{17}$,Val$^{26}$,Thr$^{28}$]-VIP
Ac-[Ala$^{9}$,Lys$^{12}$,Nle$^{17}$,Val$^{26}$,Thr$^{28}$]-VIP
Ac-[Ala$^{8}$,Lys$^{12}$,Nle$^{17}$,Val$^{26}$,Thr$^{28}$]-VIP
Ac-[Ala$^{7}$,Lys$^{12}$,Nle$^{17}$,Val$^{26}$,Thr$^{28}$]-VIP
Ac-[Ala$^{6}$,Lys$^{12}$,Nle$^{17}$,Val$^{26}$,Thr$^{28}$]-VIP
Ac-[Ala$^{5}$,Lys$^{12}$,Nle$^{17}$,Val$^{26}$,Thr$^{28}$]-VIP
Ac-[Ala$^{3}$,Lys$^{12}$,Nle$^{17}$,Val$^{26}$,Thr$^{28}$]-VIP
Ac-[Ala$^{2}$,Lys$^{12}$,Nle$^{17}$,Val$^{26}$,Thr$^{28}$]-VIP
Ac-[Ala$^{1}$,Lys$^{12}$,Nle$^{17}$,Val$^{26}$,Thr$^{28}$]-VIP
Ac-[Gly$^{1}$,Lys$^{12}$,Nle$^{17}$,Val$^{26}$,Thr$^{28}$]-VIP
Ac-[Leu$^{5}$,Lys$^{12}$,Nle$^{17}$,Val$^{26}$,Thr$^{28}$]-VIP
Ac-[1-Nal$^{6}$,Lys$^{12}$,Nle$^{17}$,Val$^{26}$,Thr$^{28}$]-VIP
Ac-[p-F-Phe$^{6}$,Lys$^{12}$,Nle$^{17}$,Val$^{26}$,Thr$^{28}$]-VIP
Ac-[Glu$^{8}$,Lys$^{12}$,Nle$^{17}$,Val$^{26}$,Thr$^{28}$]-VIP
Ac-[2-Nal$^{10}$,Lys$^{12}$,Nle$^{17}$,Val$^{26}$,Thr$^{28}$]-VIP
Ac-[p-NH$_2$-Phe$^{10}$,Lys$^{12}$,Nle$^{17}$,Val$^{26}$,Thr$^{28}$]-VIP
Ac-[O-CH$_3$-Tyr$^{10}$,Lys$^{12}$,Nle$^{17}$,Val$^{26}$,Thr$^{28}$]-VIP
Ac-[Lys$^{12}$,Nle$^{17}$,m-F-Tyr$^{22}$,Val$^{26}$,Thr$^{28}$]-VIP
Ac-[Lys$^{12}$,Nle$^{17}$,Val$^{26}$,Thr$^{28}$,Gly$^{29,30}$,Met$^{31}$]-VIP
Ac-[Lys$^{12}$,Nle$^{17}$,Val$^{26}$,Thr$^{28}$,Gly$^{29,30}$,Cys(Acm)$^{31}$]-VIP
Ac-[Lys$^{12}$,Nle$^{17}$,Val$^{26}$,Thr$^{28}$,Gly$^{29,30}$,Thr$^{31}$]-VIP
Ac-[Lys$^{12}$,Nle$^{17}$,Val$^{26}$,Thr$^{28}$,Ala$^{29,30}$,Met$^{31}$]-VIP
Ac-[Lys$^{12}$,Nle$^{17}$,Val$^{26}$,Thr$^{28}$,Ala$^{29-31}$]-VIP
Ac-[Lys$^{12}$,Nle$^{17}$,Val$^{26}$,Thr$^{28}$,Gly$^{29}$,Lys$^{30}$]-VIP
Ac-[Lys$^{12,14}$,Nle$^{17}$,Ala$^{19}$,Val$^{26}$,Thr$^{28}$]-VIP
Ac-[2-Nal$^{10}$,Lys$^{12}$,Ala$^{17}$,Val$^{26}$,Thr$^{28}$]-VIP
Ac-[Glu$^{8}$,Lys$^{12}$,Nle$^{17}$,Val$^{26}$,Thr$^{28}$,Ala$^{29,30}$,Met$^{31}$]-VIP
Ac-[Glu$^{8}$,Lys$^{12}$,Nle$^{17}$,Val$^{26}$,Thr$^{28}$,Phe$^{31}$]-VIP
Ac-[p-F-Phe$^{6}$,Glu$^{8}$,Lys$^{12}$,Nle$^{17}$,Ala$^{19}$,Val$^{26}$,Thr$^{28}$,Gly$^{29,30}$,Cys(Acm)$^{31}$]-VIP
Ac-[p-F-Phe$^{6}$,p-NH$_2$-Phe$^{10}$,Lys$^{12}$,Nle$^{17}$,Val$^{26}$,Thr$^{28}$]-VIP
Ac-[Lys$^{12}$,Ala$^{17}$,Val$^{26}$,Thr$^{28}$,Gly29,30,Cys(Acm)$^{31}$]-VIP
Ac-[Glu$^{8}$,Lys$^{12,14}$,Nle$^{17}$,Val$^{26}$,Thr$^{28}$,Gly$^{29,30}$,Met$^{31}$]-VIP
Ac-[p-NH$_2$-Phe$^{10}$, Lys$^{12}$,Nle$^{17}$,Ala$^{19}$,Val$^{26}$,Thr$^{28}$]-VIP
Ac-[p-F-Phe$^{6}$,Glu$^{8}$,Lys$^{12}$,Nle$^{17}$,Val$^{26}$,Thr$^{28}$,Gly$^{29,30}$,Cys(Acm)$^{31}$]-VIP
Ac-[Glu$^{8}$,Lys$^{12}$,Ala$^{17,19}$,Val$^{26}$,Thr$^{28}$,Gly$^{29,30}$,Met$^{31}$]-VIP
Ac-[Glu$^{8}$,Lys$^{12}$,Nle$^{17}$,Val$^{26}$,Thr$^{28}$,Gly$^{29,30}$,Ala$^{31}$]-VIP
Ac-[Glu$^{8}$,Lys$^{12}$,Nle$^{17}$,Ala$^{19}$,Val$^{26}$,Thr$^{28}$,Gly$^{29,30}$,Met$^{31}$]-VIP
Ac-[p-F-Phe$^{6}$,Lys$^{12}$,Nle$^{17}$,Ala$^{19}$,Val$^{26}$,Thr$^{28}$,Gly$^{29,30}$,Cys(Acm)$^{31}$]-VIP
Ac-[Glu$^{8}$,Lys$^{12}$,Nle$^{17}$,Val$^{26}$,Thr$^{28}$,Gly$^{29,30}$,Ser$^{31}$]-VIP
Ac-[p-F-Phe$^{6}$,Glu$^{8}$,Lys$^{12}$,Nle$^{17}$,Ala$^{19}$,Val$^{26}$,Thr$^{28}$]-VIP
Ac-[Glu$^{8}$,Orn$^{12}$,Nle$^{17}$,Val$^{26}$,Thr$^{28}$]-VIP
Ac-[Lys$^{12}$,Nle$^{17}$,Ala$^{25}$,Leu$^{26}$,Lys$^{27,28}$,Gly$^{29,30}$,Thr$^{31}$]-VIP
Ac-[Glu$^{8}$,Lys$^{12}$,Nle$^{17}$,Val$^{26}$,Thr$^{28}$,Ala$^{29-31}$]-VIP
Ac-[Lys$^{12}$,Ala$^{17,19}$,Val$^{26}$,Thr$^{28}$]-VIP
Ac-[Glu$^{8}$,Lys$^{12}$,Nle$^{17}$,Val$^{26}$,Thr$^{28}$,Gly$^{29}$,Lys$^{30}$]-VIP
Ac-[p-HN$_2$-Phe$^{10}$,Lys$^{12}$,Nle$^{17}$,Val$^{26}$,Thr$^{28}$,Gly$^{29,30}$,Cys(Acm)$^{31}$]-VIP
Ac-[Glu$^{8}$,Lys$^{12}$,Nle$^{17}$,Val$^{26}$,Thr$^{28}$,Gly$^{29,30}$,Cys(Acm)$^{31}$]-VIP
Ac-[Glu$^{8}$,Lys$^{12}$,Nle$^{17}$,Val$^{26}$,Thr$^{28}$,Gly$^{29,30}$,Met$^{31}$]-VIP
CH$_3$S(CH$_2$)$_2$CO-[Lys$^{12}$,Nle$^{17}$,Val$^{26}$,Thr$^{28}$]-VIP(2-28)
CH$_3$SO(CH$_2$)$_2$CO-[Lys$^{12}$,Nle$^{17}$,Val$^{26}$,Thr$^{28}$]-VIP(2-28)
Ac-[N-CH$_3$-Ala$^{1}$,Lys$^{12}$,Nle$^{17}$,Val$^{26}$,Thr$^{28}$]-VIP
Ac-[Leu$^{5}$,Orn$^{12}$,Ala$^{17,19}$,Thr$^{25}$,Val$^{26}$,Thr$^{28}$,Gly$^{29,30}$,Cys(Acm)$^{31}$]-VIP
Ac-[p-F-Phe$^{6}$,2-Nal$^{10}$,Lys$^{12}$,Nle$^{17}$,Val$^{26}$,Thr$^{28}$,Gly$^{29,30}$,Met$^{31}$]-VIP
Ac-[p-F-Phe$^{6}$,Glu$^{8}$,Lys$^{12,14}$,Nle$^{17}$,Ala$^{19}$,Val$^{26}$,Thr$^{28}$,Gly$^{29,30}$,Cys(Acm)$^{31}$]-VIP Particularly preferred compounds of the present invention are:
Ac-[p-F-Phe$^{6}$,Lys$^{12}$,Nle$^{17}$,Ala$^{19}$,Val$^{26}$,Thr$^{28}$Gly$^{29,30}$,Cys(Acm)$^{31}$]-VIP
Ac-[Leu$^{5}$,Orn$^{12}$,Ala$^{17}$Thr$^{25}$,Val$^{26}$,Thr$^{28}$Gly$^{29-30}$,Cys(Acm)$^{31}$]-VIP
Ac-[p-F-Phe$^{6}$,Glu$^{8}$,Lys$^{12}$,Nle$^{17}$,Ala$^{19}$,Val$^{26}$,Thr$^{28}$,Gly$^{29,30}$,Cys(Acm)$^{31}$]-VIP
Ac-[N-Me-Ala$^{1}$,Lys$^{12}$,Nle$^{17}$,Val$^{26}$,Thr$^{28}$]-VIP
Ac-[p-F-Phe$^{6}$,p-NH$_2$-Phe$^{10}$,Lys$^{12}$,Nle$^{17}$,Val$^{26}$,Thr$^{28}$]-VIP
Ac-[Glu$^{8}$,Lys$^{12}$,Nle$^{17}$,Val$^{26}$,Thr$^{28}$,Gly$^{29,30}$,Met$^{31}$]-VIP
Ac-[p-NH$_2$-Phe$^{10}$,Lys$^{12}$,Nle$^{17}$,Val$^{26}$,Thr$^{28}$]-VIP
Ac-[Glu$^{8}$,Lys$^{12}$,Nle$^{17}$,Val$^{26}$,Thr$^{28}$,Gly$^{29,30}$,Cys(Acm)$^{31}$]-VIP The above representative compounds may be readily synthesized by any known conventional procedure for the formation of a peptide linkage between amino acids. Such conventional procedures include, for example, any solution phase procedure permitting a condensation between the free alpha amino group of an amino acid or residue thereof having its carboxyl group or other reactive groups protected and the free primary carboxyl group of another amino acid or residue thereof having its amino group or other reactive groups protected.

The process for synthesizing the representive compounds may be carried out by a procedure whereby each amino acid in the desired sequence is added one at a time in succession to another amino acid or residue thereof or by a procedure whereby peptide fragments with the desired amino acid sequence are first synthesized conventionally and then condensed to provide the desired peptide.

Such conventional procedures for synthesizing the novel compounds of the present invention include for example any solid phase peptide synthesis method. In such a method the synthesis of the novel compounds can be carried out by sequentially incorporating the desired amino acid residues one at a time into the growing peptide chain according to the general principles of solid phase methods [Merrifield, R. B., J. Amer. Chem. Soc. 85, 2149–2154 (1963); Barany et al, The Peptides, Analysis, Synthesis and Biology, Vol. 2, Gross, E. and Meienhofer, J., Eds. Academic Press 1–284 (1980)].

Common to chemical syntheses of peptides is the protection of reactive side chain groups of the various amino acid moieties with suitable protecting groups which will prevent a chemical reaction from occuring at that site until the protecting group is ultimately removed. Usually also common is the protection of the alpha amino group on an amino acid or fragment while that entity reacts at the carboxyl group, followed by the selective removal of the alpha amino protecting group to allow a subsequent reaction to take place at that site. While specific protecting groups have been disclosed in regard to the solid phase synthesis method, it should be noted that each amino acid can be protected by a protective group conventionally used for the respective amino acid in solution phase synthesis.

Alpha amino groups may be protected by a suitable protecting group selected from aromatic urethane-type protecting groups, such as benzyloxycarbonyl (Z) and substituted benzyloxycarbonyl, such as p-chlorobenzyloxycarbonyl, p-nitrobenzyloxycarbonyl, p-bromobenzyl-oxycarbonyl, p-biphenyl-isopropyloxycarbonyl, 9-fluorenylmethyl-oxycarbonyl (Fmoc) and p-methoxybenzyloxycarbonyl (Moz); aliphatic urethane-type protecting groups, such as t-butyloxycarbonyl (Boc), diisopropylmethyloxycarbonyl, isopropyloxycarbonyl, and allyloxycarbonyl. Boc is most preferred for alpha amino protection.

Carboxyl groups may be protected by a suitable protecting group selected from aromatic esters such as benzyl (OBzl) or benzyl substituted with lower alkyl, halo, nitro, thio, or substituted thio, i.e., lower alkyl (1-7 carbon atoms)thio; aliphatic esters such as lower alkyl, t-butyl (To-Bu), cyclopentyl, cyclohexyl (OcHx), cycloheptyl, and 9-fluorenylmethyl (OFm). OBzl is most preferred for glutamic acid (Glu). OcHx and OBzl are most preferred for aspartic acid (Asp).

Hydroxyl groups may be protected by a suitable protecting group selected from ethers such as benzyl (Bzl) or benzyl substituted with lower alkyl, halo, such as 2,6-dichlorobenzyl (DCB), nitro, or methoxy; t-butyl (t-Bu), tetrahydropyranyl, and triphenylmethyl (trityl). Bzl is most preferred for serine (Ser) and threonine (Thr). Bzl and DCB are most preferred for tyrosine (Tyr).

Side chain amino groups may be protected by a suitable protecting group selected from aromatic urethane-type protecting groups such as benzyloxycarbonyl (Z) and substituted benzyloxycarbonyl, such as p-chlorobenzyloxycarbonyl, 2-chlorobenzyloxycarbonyl (2-Cl-Z), p-nitro-benzyloxycarbonyl, p-bromobenzyloxycarbonyl, p-biphenyl-isopropyl-oxycarbonyl, 9-fluorenylmethyloxycarbonyl (Fmoc) and p-methoxybenzyloxycarbonyl (Moz); aliphatic urethane-type Protecting groups, such as t-butyloxycarbonyl (Boc), diisopropylmethyloxycarbonyl, isopropyloxycarbonyl, and allyloxycarbonyl. Z is most preferred for ornithine (Orn). 2-Cl-Z is most preferred for lysine (Lys).

Guanidino groups may be protected by a suitable protecting group selected from nitro, p-toluenesulfonyl (Tos), Z, adamantyloxycarbonyl, and Boc. Tos is most preferred for arginine (Arg).

Side chain amide groups may be protected by xanthyl (Xan) No protection is preferred for asparagine (Asn) and glutamine (Gln).

Imidazole groups may be protected by a suitable protecting group selected from p-toluenesulfonyl (Tos), 9-fluorenylmethyloxycarbonyl (Fmoc), triphenylmethyl (trityl), 2,4-dinitrophenyl (Dnp), Boc and benzyloxymethyl (Bom). Tos is most preferred for histidine (His).

All solvents, isopropanol (iPrOH), methylene chloride (CH$_2$Cl$_2$), and dimethylformamide (DMF) were purchased additional distillation. Trifluoroacetic acid was purchased from Halocarbon and used without further purification. Diisopropylethylamine (DIPEA) was purchased from Pfaltz and Bauer and distilled from CaO and ninhydrin prior to use. Dicyclohexylcarbodiimide (DCC) and diisopropylcarbodiimide (DIC) were purchased from Fluka and used without further purification. Hydroxybenzotriazole (HOBT) and 1,2-ethanedithiol (EDT) were purchased from Sigma Chemical Co. and used without further purification. Protected amino acids were generally of the L configuration and were obtained from Chemical Dynamics Corp. or Bachem. Purity of these reagents were confirmed by thin layer chromatography, NMR and melting point prior to use. Benzhydrylamine resin (BHA) was a copolymer of styrene—1% divinylbenzene (100-200 or 200-400 mesh) obtained from Biomega, Bachem, Omni or Advanced Chemtech. Total nitrogen content of these resins were generally between 0.3 and 0.7 meq/g.

Thin layer chromatography (TLC) was performed on glass backed precoated silica gel 60 F254 plates (Merck) using appropriate solvent systems. Detection of compounds was performed by UV fluorescence quenching (254 nm absorption), iodine staining, or ninhydrin spray (for primary and secondary amines).

For amino acid composition analyses, peptides were hydrolyzed in 6N HCl, containing 1-4 mg of phenol, at 115° C. for 22-24 hours in sealed, evacuated hydrolysis tubes Analyses were performed on either a Beckman 121M amino acid analyzer or a Waters HPLC-based amino acid analysis system using either a Waters Cat Ex resin or a Pierce AA511 column and ninhydrin detection.

High performance liquid chromatography (HPLC) was conducted on an LDC apparatus consisting of Constametric I and III pumps, a Gradient Master solvent programmer and mixer, and a Spectromonitor III variable wavelength UV detector. Analytical HPLC was performed in reversed phase mode using Waters mBondapak C$_{18}$ columns (0.4×30 cm). Preparative HPLC separations were run on Whatman Magnum 20 partisil 10 ODS-3 columns (2×25 cm or 2×50 cm) equipped with a Waters Guard-Pak C$_{18}$ precolumn.

Peptides were preferably prepared using solid phase synthesis by the method generally described by Merrifield, [J. Amer. Chem. Soc., 85, 2149 (1963)], although other equivalent chemical synthesis known in the art could be used as previously mentioned. Solid phase synthesis is commenced from the C-terminal end of the peptide by coupling a protected alpha-amino acid to a suitable resin. Such a starting material can be prepared by attaching an alpha-amino-protected amino acid by an ester linkage to a chloromethylated resin or a hydroxymethyl resin, or by an amide bond to a benzhydrylamine (BHA) or para-methylbenzhydrylamine (MBHA) resin Preparation of the hydroxymethyl resin is well known in the art. Chloromethylated resins are commercially available and the preparation is also well known in the art. BHA and MBHA resin supports are commercially available and generally used when the desired peptide being synthesized has an unsubstituted amide at the C-terminus.

In general, the first amino acid to be coupled onto the BHA resin was added as the Boc-amino acid symmetrical anhydride, using 2-10 equivalents of activated amino acid per resin nitrogen equivalent. After coupling the resin was washed and dried under vacuum. Loading of the amino acid onto the resin may be determined by amino acid analysis of an aliquot of Boc-amino acid resin. Loadings generally ranged from 0.2 to 0.4 mmol/g resin. Any unreacted amino groups, may be capped by reacting the resin with acetic anhydride and diispropylethylamine in methylene chloride Following addition of the Boc-amino acid, the resins were carried through several repetitive cycles to add amino acids sequentially. The alpha amino Boc protection was removed under acidic conditions. Trifluoroacetic acid (TFA) in methylene chloride, HCl in dioxane or formic acid/acetic acid mixtures may be used for this purpose. Preferably 50% TFA in methylene chloride (v/v) is utilized. This may also contain 1-5% by volume of EDT or dimethylsulfide as a scavenger for t-butyl carbonium ions. Other standard cleavage reagents as known in the art may also be used.

Following the removal of the alpha amino protecting group, the subsequent protected amino acids are coupled stepwise in the desired order to obtain an intermediate, protected peptide-resin. The activating reagents used for coupling of the amino acids in the solid phase synthesis of the peptides are well known in the art. For example, appropriate reagents for such syntheses are benzotriazol-1-yloxy-tri-(dimethylamino)phosphonium hexafluorophosphate (BOP), dicyclohexylcarbodiimide (DCC), and diisopropylcarbodiimide (DIC). Preferred here are DCC and DIC. Other activating agents are described by Barany and Merrifield [in The Peptides, Vol. 2, J. Meienhofer, ed., Academic Press, 1979, pp 1-284] may be utilized. Various reagents such as 1 hydroxybenzotriazole (HOBT), N-hydroxysuccinimide (HOSu) and 3,4-dihydro-3-hydroxy-4-oxo-1,2,3-benzotriazine (HOOBT) may be added to the coupling mixtures in order to optimize the synthetic cycles. Preferred here is HOBT.

The protocol for a typical synthetic cycle was as follows:

TABLE 1

| Step | Reagent | Time |
|---|---|---|
| 1 | $CH_2Cl_2$ | 2 × 30 sec |
| 2 | 50% $TFA/CH_2Cl_2$ | 1 min |
| 3 | 50% $TFA/CH_2Cl_2$ | 15 min |
| 4 | $CH_2Cl_2$ | 2 × 30 sec |
| 5 | iPrOH | 2 × 30 sec |
| 6 | $CH_2Cl_2$ | 4 × 30 sec |
| 7 | 6% $DIPEA/CH_2Cl_2$ | 3 × 2 min |
| 8 | $CH_2Cl_2$ | 3 × 30 sec |
| 9 | coupling | 1-18 hours |
| 10 | $CH_2Cl_2$ | 2 × 30 sec |
| 11 | iPrOH | 1 × 10 sec |
| 12 | $CH_2Cl_2$ | 1 × 30 sec |
| 13 | DMF | 2 × 30 sec |
| 14 | $CH_2Cl_2$ | 3 × 30 sec |

Solvents for all washings and couplings were measured to volumes of 10-40 ml/g resin. Couplings were performed using either the preformed symmetrical anhydrides of the Boc-amino acids or as the O-acyl isourea derivatives. Generally, 2-10 equivalents of activated Boc-amino acid was added per equivalent of amine resin using methylene chloride as solvent. Boc-Arg(Tos), Boc-Gln, Boc-Asn, and Boc-His(Tos) were coupled in 20-25% $DMF/CH_2Cl_2$. Boc-Asn and Boc-Gln were coupled as their HOBT active esters in order to minimize known side reactions.

Coupling reactions were monitored by the Kaiser ninhydrin test to determine extent of completion [Kaiser et at., Anal. Biochem., 34, 595-598 (1970)]. Slow reaction kinetics were observed for Boc-Arg(Tos), Boc-Asn, and Boc-Gln. Any incomplete coupling reactions were either recoupled with freshly prepared activated amino acid or capped by treating the peptide resin with acetic anhydride as described above. The fully assembled peptide-resins were dried in vacuo for several hours.

For each compound, the blocking groups were removed and the peptide cleaved from the resin by the following procedure. Generally, the peptide-resins were treated with 25-100 mL ethanedithiol, 1 mL anisole, and 9 mL liquid hydrogen fluoride, per gram of resin, at 0° C. for 45-60 min, in a Teflon HF apparatus (Peninsula). Alternatively, a modified two step cleavage procedure [Tam et al., Tetrahedron Letters, 23, 2939-2940 (1982)] could be used wherein the peptide-resin was treated with 3 mL dimethyl sulfide and 1 mL hydrogen fluoride for 2 hours at 0° C. and evaporated prior to the 90% HF treatment. Volatile reagents were then removed under vacuum at ice bath temperature. The residue was washed with two or three 30 mL volumes each of $Et_2O$ and EtOAc and filtered. The peptides were extracted from the resin by washing with 4×20 mL 10% AcOH and filtered. The combined aqueous filtrates were lyophilized to yield the final crude product.

Purifications were generally carried out directly on the crude peptide by preparative HPLC. The peptides were applied to the columns in a minimum volume of either 1% AcOH or 0.1% TFA. Gradient elution was generally started at 10% B buffer, 10%-25% B in 10 minutes, and 25-35% B in 3 hours (buffer A: 0.1% $TFA/H_2O$, buffer B: 0.1% $TFA/CH_3CN$) at a flow rate of 8.0 mL/min. UV detection was made at 220 nm. Fractions were collected at 1.5-2.5 minute intervals and inspected by analytical HPLC. Fractions judged to be of high purity were pooled and lyophilized.

Purity of the final products were checked by analytical HPLC on a reversed phase column as stated above. Generally, a gradient elution of 20-40% B (buffer A: 0.022% $TFA/H_2O$, buffer B: 0.022% $TFA/CH_3CN$) in 15 minutes at 2.0 mL/min. UV detection was at 210 nm. Purity of all products was judged to be approximately 97-99%. Amino acid analyses of the individual peptides were performed and the values obtained were within acceptable limits. In general, all final products were also subjected to fast atom bombardment mass spectrometry (FAB-MS). All products yielded the expected parent M+H ions within acceptable limits.

The novel compounds of the present invention have valuable pharmacological properties. It will be shown that they are potent bronchodilators having no cardiovascular side effects. Thus being highly active bronchodilators, the compounds are valuable pharmaceutical agents for treatment of bronchoconstrictive disorders, e.g. asthma.

The novel compounds of formula I may be combined with various typical pharmaceutical carriers to provide compositions suitable for use in the treatment of bronchoconstrictive disorders such as asthma. The dosage of these compounds is dependant upon various factors such as the particular compound employed and the particular formulation. An effective dosage can be determined by one of ordinary skill in the art from the effective concentration ($EC_{50}$) disclosed herein.

Novel compounds of formula I form pharmaceutically acceptable acid addition salts with a variety of inorganic and organic acids such as sulfuric, phosphoric, hydrochloric, hydrobromic, hydroiodic, nitric, sulfamic, citric, lactic, pyruvic, oxalic, maleic, succinic, tartaric, cinnamic, acetic, trifluoroacetic, benzoic, salicylic, gluconic, ascorbic, and related acids.

The instant compounds may be administered by parenteral application either intravenously, subcutaneously, intramuscularly, orally, or intranasally. A preferred route for parenteral administration is by aerosol via oral or intranasal administration.

The present invention will be further described in connection with the following examples which are set forth for the purposes of illustration only.

EXAMPLE 1

Boc-Ala-BHA Resin

Benzhydrylamine copolystyrene-1% divinylbenzene cross-linked resin (3.0 g, 2.1 milliequiv, 100–200 ASTM mesh, Omni Biochem) was swelled in 30 mL methylene chloride, filtered and washed using steps 7–8 of the protocol in Table 1. The resin was resuspended in 30 mL methylene chloride and to this was added Boc-Ala (568 mg, 3.0 mmole) and dicyclohexylcarbodiimide (310 mg, 1.5 mmol). This mixture was shaken for 15 hours at room temperature, filtered and then protocol steps 10–14 of Table 1 were performed. Kaiser ninhydrin analysis was negative. Unreacted amine groups were capped by treating the resin with 1 mL acetic anhydride in 30 mL methylene chloride for 30 minutes, filtered and washed with protocol steps 13–14. The resin was dried under vacuum overnight to yield 3.1 g of Boc-Ala-BHA resin. A portion of this resin was subjected to amino acid analysis which indicated a loading of 0.20 mmol Ala/g.

EXAMPLE 2

Boc-Thr(Bzl)-BHA Resin 10.0 g (7.0 mequiv) of benzhydrylamine resin (100–200 ASTM mesh, Omni) was treated as in Example 1 except that the resin was coupled with Boc-Thr(Bzl) (3.1 g, 10.0 mmole) and dicyclohexylcarbodiimide (1.0 g, 5.0 mmole). The resin was dried under vacuum to yield 10.9 g of Boc-Thr(Bzl)-BHA resin. Amino acid analysis indicated a loading of 0.2 mmol Thr/g.

EXAMPLE 3

Boc-Ser(Bzl)-BHA Resin 0.75 g (0.53 mequiv) of benzhydrylamine resin (100–200 ASTM mesh, Omni) was treated as in Example 1 except that the resin was coupled with Boc-Ser(Bzl) (222 mg, 0.75 mmole) and dicyclohexylcarbodiimide (77 mg, 0.375 mmole). The resin was dried under vacuum to yield 0.80 g of Boc-Ser(Bzl)-BHA resin. Amino acid analysis indicated a loading of 0.16 mmol Ser/g.

EXAMPLE 4

Boc-Met-BHA Resin 0.75 g (0.53 mequiv) of benzhydrylamine resin (100–200 ASTM mesh, Omni) was treated as in Example 1 except that the resin was coupled with Boc-Met (187 mg, 0.75 mmole) and dicyclohexylcarbodiimide (77 mg, 0.375 mmole). The resin was dried under vacuum to yield 0.81 g of Boc-Met-BHA resin. Amino acid analysis indicated a loading of 0.19 mmole Met/g.

EXAMPLE 5

Ac-[Lys$^{12}$,Nle$^{17}$,Val$^{26}$,Ala$^{28}$]-VIP

A 0.253 g (0.05 mmol) portion of Boc-Ala-BHA resin from Example 1 was subjected to solid phase synthesis using the above stated protocol. All couplings were performed using equal molar equivalents of Boc-amino acid and diisopropylcarbodiimide. Boc-asparagine and Boc-glutamine were incorporated as the respective active esters by addition of 1.5 molar excess HOBT to the coupling mixture. Reaction times were generally 2–18 hours for completion of the coupling step. Twenty-seven coupling cycles were performed of one cycle each with Boc-Leu (124 mg, 0.5 mmol), Boc-Val (109 mg, 0.5 mmol), Boc-Ser(Bzl) (147 mg, 0.5 mmol), Boc-Asn (116 mg, 0.5 mmol), Boc-Leu (124 mg, 0.5 mmol), Boc-Tyr(2,6-DCB) (220 mg, 0.5 mmol), Boc-Lys(2-Cl-Z) (207 mg, 0.5 mmol), Boc-Lys(2-Cl-Z) (207 mg, 0.5 mmol), Boc-Val (109 mg, 0.5 mmol), Boc-Ala (95 mg, 0.5 mmol), Boc-Nle (116 mg, 0.5 mmol), Boc-Gln (123 mg, 0.5 mmol), Boc-Lys(2-Cl-Z) (207 mg, 0.5 mmol), Boc-Arg(Tos) (214 mg, 0.5 mmol), Boc-Leu (124 mg, 0.5 mmol), Boc-Lys(2-Cl-Z) (207 mg, 0.5 mmol), Boc-Thr(Bzl) (154 mg, 0.5 mmol), Boc-Tyr(2,6-DCB) (220 mg, 0.5 mmol), Boc-Asn (116 mg, 0.5 mmol), Boc-Asp(OcHx) (158 mg, 0.5 mmol), Boc-Thr(Bzl) (154 mg, 0.5 mmol), Boc-Phe (133 mg, 0.5 mmol), Boc-Val (108 mg, 0.5 mmol), Boc-Ala (95 mg, 0.5 mmol), Boc-Asp(OcHx) (158 mg, 0.5 mmol), Boc-Ser(Bzl) (148 mg, 0.5 mmol), and Boc-His(Tos) (204 mg, 0.5 mmol). The peptide-resin was then carried through protocol steps 1–8 and reacted twice with 0.5 mL acetic anhydride and 167 mL DIPEA in 10 mL methylene chloride for 50 minutes. The resin was washed using steps 10–14 and dried under vacuum to yield 407 mg.

The peptide resin was deblocked and cleaved by treatment with 10 mL liquid HF containing 1 mL anisole and 100 mL ethanedithiol for 1 hour at 0° C. The reaction mixture was evaporated to dryness under vacuum, washed with 2×30 mL Et$_2$O, and extracted with 3×30 mL 10% AcOH. The aqueous filtrate was lyophilized to yield 135 mg of a white powder.

The crude peptide was purified by preparative HPLC. It was applied to a Whatman Magnum-20 ODS-3 column (2×50 cm) and eluted with a linear gradient of 25–35% B (buffer A: 0.1% TFA/H$_2$O, buffer B: 0.1% TFA/CH$_3$CN) in 3 hours at 8.0 mL/min. The main peak was cut by analytical HPLC analysis of collected fractions, pooled and lyophilized to yield 26.6 mg of a white, amorphous powder. This compound was homogeneous by HPLC and gave a correct amino acid analysis. FAB-MS: MH calc. 3265.8, found 3266.5.

EXAMPLE 6

Ac-[Lys$^{12}$,Nle$^{17}$,Val$^{26}$,Ala$^{27}$,Thr$^{28}$]-VIP

A 0.25 g (0.05 mmol) portion of Boc-Thr(Bzl)-BHA resin from Example 2 was subjected to solid phase synthesis as in Example 5 except that Boc-Leu in the first cycle was replaced by Boc-Ala (95 mg, 0.5 mmol). The peptide-resin (399 mg) was deblocked to yield 117 mg of crude peptide. Purification by HPLC yielded 32.4 mg of a white, amorphous powder. The compound was homogeneous by HPLC and gave a correct amino acid analysis. FAB-MS: MH calc. 3253.7, found 3253.4.

EXAMPLE 7

Ac-[Lys$^{12}$,Nle$^{17}$,Ala$^{26}$,Thr$^{28}$]-VIP

A 0.254 g (0.05 mmol) portion of Boc-Thr(Bzl)-BHA resin from Example 2 was subjected to solid phase synthesis as in Example 5 except that Boc-Val in the second cycle was replaced by Boc-Ala (95 mg, 0.5 mmol). The peptide-resin (399 mg) was deblocked to yield 100 mg of crude peptide. Purification by HPLC yielded 29.4 mg of a white, amorphous powder. The compound was homogeneous by HPLC and gave a correct amino acid analysis. FAB-MS: MH calc. 3267.8, found 3267.5.

EXAMPLE 8

Ac-[Lys$^{12}$,Nle$^{17}$,Ala$^{25}$,Val$^{26}$,Thr$^{28}$]-VIP

A 0.25 g (0.05 mmol) portion of Boc-Thr(Bzl)-BHA resin from Example 2 was subjected to solid phase synthesis as in Example 5 except that Boc-Ser(Bzl) in the third cycle was replaced by Boc-Ala (95 mg, 0.5 mmol). The peptide-resin (394 mg) was deblocked to yield 125 mg of crude peptide. Purification by HPLC yielded 31.9 mg of a white, amorphous powder. The compound was homogeneous by HPLC and gave a correct amino acid analysis. FAB-MS: MH calc. 3279.8, found 3279.8.

EXAMPLE 9

Ac-[Lys$^{12}$,Nle$^{17}$,Ala$^{26}$,Val$^{26}$,Thr$^{28}$]-VIP

A 0.25 g (0.05 mmol) portion of Boc-Thr(Bzl)-BHA resin from Example 2 was subjected to solid phase synthesis as in Example 5 except that Boc-Asn in the fourth cycle was replaced by Boc-Ala (95 mg, 0.5 mmol). The peptide-resin (373 mg) was deblocked to yield 83.5 mg of crude peptide. Purification by HPLC yielded 28.7 mg of a white, amorphous powder. The compound was homogeneous by HPLC and gave a correct amino acid analysis. FAB-MS: MH calc. 3252.8, found 3252.1.

EXAMPLE 10

Boc-Thr(Bzl)-BHA Resin

Benzhydrylamine copolystyrene-1% divinylbenzene cross-linked resin (5.0 g, 2.6 mequiv, 200-400 ASTM mesh, Vega Biochem) was swelled in 50 mL methylene chloride, filtered and washed using steps 7-8 of the protocol in Table 1. The resin was resuspended in 60 mL methylene chloride and to this was added Boc-Thr(Bzl) (2.32 g, 7.5 mmole) and dicyclohexylcarbodiimide (774 mg, 3.75 mmole). This mixture was shaken for 4 hours at room temperature, filtered and then protocol steps 10-14 of Table 1 were performed. Kaiser ninhydrin analysis was negative. Unreacted amine groups were capped by treating the resin with 5 mL acetic anhydride and 5 mL DIPEA in 50 mL methylene chloride for 60 minutes, filtered and washed with protocol steps 13-14. The resin was dried under vacuum overnight to yield 5.8 g of Boc-Thr(Bzl)-BHA resin. A portion of this resin was subjected to amino acid analysis which indicated a loading of 0.276 mmol Thr/g.

EXAMPLE 11

Ac-[Lys$^{12}$, Nle$^{17}$, Ala$^{23}$, Val$^{26}$, Thr$^{28}$]-VIP

A 1.0 g (0.27 mmol) portion of Boc-Thr(Bzl)-BHA resin from Example 10 was subjected to solid phase synthesis on an Applied Biosystems model 430A peptide synthesizer. All couplings were performed using preformed symmetrical anhydrides prepared from Boc-amino acid and dicyclohexylcarbodiimide. Boc-asparagine, Boc-glutamine, and Boc-arginine(tosyl) were routinely double coupled as the respective HOBT active esters. Twenty-seven coupling cycles were performed of one cycle each with Boc-Leu (499 mg, 2.0 mmol), Boc-Val (435 mg, 2.0 mmol), Boc-Ser(Bzl) (590 mg, 2.0 mmol), Boc-Asn (464 mg, 2.0 mmol), Boc-Ala (378 mg, 2.0 mmol), Boc-Tyr(2,6-DCB) (880 mg, 2.0 mmol), Boc-Lys(2-Cl-Z) (830 mg, 2.0 mmol), Boc-Lys(2-Cl-Z) (830 mg, 2.0 mmol), Boc-Val (435 mg, 2.0 mmol), Boc-Ala (378 mg, 2.0 mmol), Boc-Nle (462 mg, 2.0 mmol), Boc-Gln (492 mg, 2.0 mmol), Boc-Lys(2-Cl-Z) (830 mg, 2.0 mmol), Boc-Arg(Tos) (856 mg, 2.0 mmol), Boc-Leu (499 mg, 2.0 mmol), Boc-Lys(2-Cl-Z) (830 mg, 2.0 mmol), Boc-Thr(Bzl) (618 mg, 2.0 mmol), Boc-Tyr(2,6-DCB) (880 mg, 2.0 mmol), Boc-Asn (464 mg, 2.0 mmol), Boc-Asp(OcHx) (630 mg, 2.0 mmol), Boc-Thr(Bzl) (618 mg, 2.0 mmol), Boc-Phe (530 mg, 2.0 mmol), Boc-Val (435 mg, 2.0 mmol), Boc-Ala (378 mg, 2.0 mmol), Boc-Asp(OcHx) (630 mg, 2.0 mmol), Boc-Ser(Bzl) (590 mg, 2.0 mmol), and Boc-His(Tos) (819 mg, 2.0 mmol). The peptide resin was removed from the synthesizer and carried through protocol steps 1-8 and reacted with 1.0 mL acetic anhydride in 20 mL 6% DIPEA/methylene chloride for 30 minutes. The resin was washed with steps 10-14 and dried under vacuum to yield 2.25 g of peptide resin.

A 1.5 g (0.18 mmol) portion of this resin was treated with 6 mL dimethylsulfide and 2 mL liquid HF for 2 hours and 0° C. The reaction mixture was evaporated and the residue was treated with 1 mL anisole and 9 mL liquid HF for 45 minutes at 0° C. The reaction mixture was evaporated and the residue was washed with 2×30 mL Et$_2$O and 4×30 mL EtOAc. The resin was extracted with 3×15 mL 10% AcOH and 2×20 mL H$_2$O. The combined aqueous filtrates were lyophilized to yield 800 mg of a white solid.

A 400 mg (0.09 mmol) portion of this material was purified by preparative HPLC as in Example 5 except that a linear gradient of 10-40% in 3 hours was run. The main peak was cut by analytical HPLC analysis of collected fractions, pooled and lyophilized to yield 47.0 mg of a white, amorphous powder. This compound was homogeneous by HPLC and gave a correct amino acid analysis.

EXAMPLE 12

Ac-[Lys$^{12}$, Nle$^{17}$, Ala$^{22}$, Val$^{26}$, Thr$^{28}$]-VIP

A 0.75 g (0.2 mmol) portion of Boc-Thr(Bzl)-BHA resin from Example 10 was subjected to solid phase synthesis on an Applied Biosystems model 430A peptide synthesizer as in Example 11. All couplings were performed as in Example 11 except that Boc-Leu (499 mg, 2.0 mmol) and Boc-Ala (378 mg, 2.0 mmol) were substituted for Boc-Ala and Boc-Tyr(2,6-DCB) in cycles 5 and 6, respectively. The peptide resin was removed from the synthesizer, deblocked with protocol steps 1-8 and treated with acetic anhydride as in Example 11. The resin was washed with steps 10-14 and dried under vacuum to yield 1.6 g of peptide resin.

A 0.8 g (0.1 mmol) portion of this resin was treated with HF as in Example 11 to yield, after lyophilization, 400 mg of a white solid. This crude peptide was purified by preparative HPLC as in Example 11 except that a linear gradient of 25-35% was run. The main peak was cut by analytical HPLC analysis of collected fractions, pooled and lyophilized to yield 17.3 mg of a white, amorphous powder. This compound was homogeneous by HPLC and gave a correct amino acid analysis. FAB-MS: calc. 3203.7, found 3203.8.

EXAMPLE 13

Ac-[Lys$^{12}$, Nle$^{17}$, Ala$^{21}$, Val$^{26}$, Thr$^{28}$]-VIP

A 0.7 g (0.19 mmol) portion of Boc-Thr(Bzl)-BHA resin from Example 10 was subjected to solid phase synthesis on an Applied Biosystems model 430A peptide synthesizer as in Example 11. All couplings were performed as in Example 11 except that Boc-Leu (499 mg, 2.0 mmol) and Boc-Ala (378 mg, 2.0 mmol) were substituted for Boc-Ala and Boc-Lys(2-Cl-Z) in cycles 5 and 7, respectively. The peptide resin was removed from the synthesizer and deblocked with protocol steps 1-8 as in Example 11 and treated with 15% acetic anhydride/methylene chloride for 15 minutes at room temperature. The resin was washed with steps 10-14 and dried under vacuum to yield 1.4 g of peptide resin.

The peptide resin was treated with HF as in Example 11 to yield, after lyophilization, 750 mg of a white solid. A 250 mg portion of this crude peptide was purified by preparative HPLC as in Example 12. The main peak was cut by analytical HPLC analysis of collected fractions, pooled and lyophilized to yield 20 mg of a white, amorphous powder. This compound was homogeneous by HPLC and gave a correct amino acid analysis.

EXAMPLE 14

Ac-[Lys$^{12}$,Nle$^{17}$,Ala$^{20}$,Val$^{26}$,Thr$^{28}$]-VIP

A 0.7 g (0.19 mmol) portion of Boc-Thr(Bzl)-BHA resin from Example 10 was subjected to solid phase synthesis on an Applied Biosystems model 430A peptide synthesizer as in Example 11. All couplings were performed as in Example 11 except that Boc-Leu (499 mg, 2.0 mmol) and Boc-Ala (378 mg, 2.0 mmol) were substituted for Boc-Ala and Boc-Lys(2-Cl-Z) in cycles 5 and 8, respectively. The peptide resin was removed from the synthesizer, deblocked with protocol steps 1-8 and treated with acetic anhydride as in Example 11. The resin was washed with steps 10-14 and dried under vacuum to yield 1.2 g of peptide resin.

The peptide resin was treated with HF as in Example 11 to yield, after lyophilization, 270 mg of a white solid. This crude peptide was purified by preparative HPLC as in Example 12. The main peak was cut by analytical HPLC analysis of collected fractions, pooled and lyophilized to yield 12.4 mg of a white, amorphous powder. This compound was homogeneous by HPLC and gave a correct amino acid analysis. FAB-MS: calc. 3238.7, found 3238.2.

EXAMPLE 15

Ac-[Lys$^{12}$,Nle$^{17}$,Ala$^{19}$,Val$^{26}$,Thr$^{28}$]-VIP

Benzhydrylamine copolystyrene-1% divinylbenzene cross-linked resin (17.7 g, 2.6 mequiv, 200-400 ASTM mesh, Vega Biochem) was swelled in 160 mL methylene chloride, filtered and washed using steps 7-8 of the protocol in Table 1. The resin was resuspended in 160 mL methylene chloride and to this was added Boc-Thr(Bzl) (6.25 g, 20.2 mmole) and dicyclohexylcarbodiimide (2.10 g, 10.1 mmol). This mixture was shaken for 8 hours at room temperature, filtered and then protocol steps 10-14 of Table 1 were performed. Kaiser ninhydrin analysis was negative. Unreacted amine groups were capped by treating the resin with 5 mL acetic anhydride and 5 mL DIPEA in 150 mL methylene chloride for 60 minutes, filtered and washed with protocol steps 13-14. The resin was dried under vacuum overnight to yield 18.0 g of Boc-Thr(Bzl)-BHA resin. A portion of this resin was subjected to amino acid analysis which indicated a loading of 0.17 mmol Thr/g.

The Boc-Thr(Bzl)-BHA resin (18.0 g, 3.06 mmol) was subjected to solid phase synthesis using the above protocol. All couplings were performed using preformed symmetrical anhydrides prepared from Boc-amino acid and dicyclohexylcarbodiimide. Boc-asparagine and Boc-glutamine were coupled as the respective HOBT active esters. Five coupling cycles were performed of one cycle each with Boc-Leu (6.1 g, 24.5 mmol), Boc-Val (5.32 g, 24.5 mmol), Boc-Ser(Bzl) (7.23 g, 24.5 mmol), Boc-Asn (3.13 g, 13.5 mmol), and Boc-Leu (6.1 g, 24.5 mmol). The resin was dried under vacuum to give 22.9 g of Boc-hexapeptide resin.

A 0.768 g (0.1 mmol) portion of this resin was carried through twenty-two coupling cycles of one cycle each with Boc-Tyr(2,6-DCB) (352 mg, 0.8 mmol), Boc-Lys(2-Cl-Z) (332 mg, 0.8 mmol), Boc-Lys(2-Cl-Z) (332 mg, 0.8 mmol), Boc-Ala (151 mg, 0.8 mmol), Boc-Ala (151 mg, 0.8 mmol), Boc-Nle (185 mg, 0.8 mmol), Boc-Gln (108 mg, 0.44 mmol), Boc-Lys(2-Cl-Z) (332 mg, 0.8 mmol), Boc-Arg(Tos) (342 mg, 0.8 mmol), Boc-Leu (199 mg, 0.8 mmol), Boc-Lys(2-Cl-Z) (332 mg, 0.8 mmol), Boc-Thr(Bzl) (247 mg, 0.8 mmol), Boc-Tyr(2,6-DCB) (352 mg, 0.8 mmol), Boc-Asn (102 mg, 0.44 mmol), Boc-Asp(OcHx) (252 mg, 0.8 mmol), Boc-Thr(Bzl) (247 mg, 0.8 mmol), Boc-Phe (212 mg, 0.8 mmol), Boc-Val (174 mg, 0.8 mmol), Boc-Ala (151 mg, 0.8 mmol), Boc-Asp(OcHx) (252 mg, 0.8 mmol), Boc-Ser(Bzl) (236 mg, 0.8 mmol), and Boc-His(Tos) (328 mg, 0.8 mmol). The peptide resin was carried through protocol steps 1-8 and treated with 1.0 mL acetic anhydride in 15 mL 6% DIPEA/methylene chloride for 30 minutes. The resin was washed using steps 10-14 and dried under vacuum to yield 1.12 g.

A 0.725 g (0.065 mmol) portion of this resin was treated as in Example 11 with 3 mL dimethylsulfide and 1 mL liquid HF for 2 hours and 0° C. The reaction mixture was evaporated and the residue was treated with 0.5 mL anisole and 4.5 mL liquid HF for 45 minutes at 0° C. The reaction mixture was evaporated and the residue was washed with 1×15 mL Et$_2$O and 3×15 mL EtOAc. The resin was extracted with 3×20 mL 10% AcOH. The combined aqueous filtrates were lyophilized to yield 367 mg of a white solid.

This crude material was purified by preparative HPLC as in Example 5 except that a linear gradient of 10-40% in 4 hours was run. The main peak was cut by analytical HPLC analysis of collected fractions, pooled and lyophilized to yield 23 mg of a white, amorphous powder. This compound was homogeneous by HPLC and gave a correct amino acid analysis.

EXAMPLE 16

Ac-[Lys$^{12}$,Ala$^{17}$,Val$^{26}$,Thr$^{28}$]-VIP

A 3.5 g (0.96 mmol) portion of Boc-Thr(Bzl)-BHA resin from Example 10 was subjected to solid phase synthesis. All couplings were performed using preformed symmetrical anhydrides prepared from Boc-amino acid and dicyclohexylcarbodiimide. Boc-asparagine and Boc-glutamine were coupled as the respective HOBT active esters. Two coupling cycles were performed of one cycle each with Boc-Leu (1.78 g, 7.7 mmol) and Boc-Val (1.68 g, 7.7 mmol) to give 3.72 g of Boc-tripeptide resin.

A 3.41 g (0.88 mmol) portion of this resin was coupled with one cycle with Boc-Ser(Bzl) (2.28 g, 7.7 mmol) to give 3.52 g of Boc-tetrapeptide resin.

A 3.2 g (0.80 mmol) portion of this resin was coupled with two cycles of one cycle each with Boc-Asn (822 mg, 3.54 mmol) and Boc-Leu (1.6 g, 6.4 mmol) to give 3.2 g of Boc-hexapeptide resin.

A 2.56 g (0.64 mmol) portion of this resin was coupled with three cycles of one cycle each with Boc-Tyr(2,6-DCB) (2.26 g, 5.1 mmol), Boc-Lys(2-Cl-Z) (2.13 g, 5.1 mmol), and Boc-Lys(2-Cl-Z) (2.13 g, 5.1 mmol) to give 3.2 g of Boc-nonapeptide resin.

A 2.8 g (0.56 mmol) portion of this resin was coupled with two cycles of one cycle each with Boc-Val (978 mg, 4.5 mmol) and Boc-Ala (851 mg, 4.5 mmol) to give 2.8 g of Boc-undecapeptide resin.

A 0.39 g (0.078 mmol) portion of this resin was coupled with seventeen cycles of one cycle each with Boc-Ala (118 mg, 0.62 mmol), Boc-Gln (85 mg, 0.34 mmol), Boc-Lys(2-Cl-Z) (260 mg, 0.62 mmol), Boc-Arg(Tos) (269 mg, 0.62 mmol), Boc-Leu (156 mg, 0.62 mmol), Boc-Lys(2-Cl-Z) (260 mg, 0.62 mmol), Boc-Thr(Bzl) (194 mg, 0.62 mmol), Boc-Tyr(2,6-DCB) (276 mg, 0.62 mmol), Boc-Asn (80 mg, 0.34 mmol), Boc-Asp(OcHx) (198 mg, 0.62 mmol), Boc-Thr(Bzl) (194 mg, 0.62 mmol), Boc-Phe (166 mg, 0.62 mmol), Boc-Val (136 mg, 0.62 mmol), Boc-Ala (119 mg, 0.62 mmol), Boc-Asp(OcHx) (198 mg, 0.62 mmol), Boc-Ser(Bzl) (185 mg, 0.62 mmol), and Boc-His(Tos) (257 mg, 0.62 mmol). The peptide resin was dried under vacuum to give 0.55 g of octacosapeptide resin. A 0.275 g (0.039 mmol) portion of this resin was treated with 0.5 mL acetic anhydride in 10 mL 6% DIPEA/methylene chloride for 30 minutes. The resin was washed with steps 10–14 and dried under vacuum to yield 0.27 g of peptide resin.

The peptide resin was treated with HF as in Example 15 to yield, after lyophilization, 139 mg of a white solid. This crude peptide was purified by preparative HPLC as in Example 15. The main peak was cut by analytical HPLC analysis of collected fractions, pooled and lyophilized to yield 6.6 mg of a white, amorphous powder. This compound was homogeneous by HPLC and gave a correct amino acid analysis.

EXAMPLE 17

Ac-[Lys$^{12}$,Ala$^{16}$,Nle$^{17}$,Val$^{26}$,Thr$^{28}$]-VIP 9.5 g (3.61 mmol) of benzhydrylamine resin (200–400 ASTM mesh, Bachem) was treated as in Example 10 except that the resin was coupled with Boc-Thr(Bzl) (3.35 g, 10.8 mmol) and dicyclohexylcarbodiimide (1.12 g, 5.42 mmol) for 18 hours. The resin was dried under vacuum overnight to yield 9.8 g of Boc-Thr(Bzl)-BHA resin. A portion of this resin was subjected to amino acid analysis which indicated a loading of 0.17 mmol Thr/g.

The Boc-Thr(Bzl)-BHA resin (9.8 g, 1.7 mmol) was subjected to solid phase synthesis using the above protocol. All couplings were performed using preformed symmetrical anhydrides prepared from Boc-amino acid and dicyclohexylcarbodiimide. Boc-asparagine and Boc-glutamine were coupled as the respective HOBT active esters. Five coupling cycles were performed of one cycle each with Boc-Leu (1.5 g, 6.0 mmol), Boc-Val (1.3 g, 6.0 mmol), Boc-Ser(Bzl) (1.8 g, 6.0 mmol), Boc-Asn (773 mg, 3.3 mmol), and Boc-Leu (1.5 g, 6.0 mmol). The resin was dried under vacuum to give 12.2 g of Boc-hexapeptide resin.

A 8.2 g (1.13 mmol) portion of this resin was coupled with six cycles of one cycle each with Boc-Tyr(2,6-DCB) (1.77 g, 4.0 mmol), Boc-Lys(2-Cl-Z) (1.67 g, 4.0 mmol), and Boc-Lys(2-Cl-Z) (1.67 g, 4.0 mmol), Boc-Val (876 mg, 4.0 mmol), Boc-Ala (762 mg, 4.0 mmol), and Boc-Nle (932 mg, 4.0 mmol) to give 10.2 g of Boc-decapeptide resin.

A 0.9 g (0.1 mmol) portion of this resin was subjected to solid phase synthesis on an Applied Biosystems model 430A peptide synthesizer as in Example 11. Sixteen coupling cycles were performed of one cycle each with Boc-Ala (378 mg, 2.0 mmol), Boc-Lys(2-Cl-Z) (830 mg, 2.0 mmol), Boc-Arg(Tos) (856 mg, 2.0 mmol), Boc-Leu (499 mg, 2.0 mmol), Boc-Lys(2-Cl-Z) (830 mg, 2.0 mmol), Boc-Thr(Bzl) (618 mg, 2.0 mmol), Boc-Tyr(2,6-DCB) (880 mg, 2.0 mmol), Boc-Asn (464 mg, 2.0 mmol), Boc-Asp(OcHx) (630 mg, 2.0 mmol), Boc-Thr(Bzl) (618 mg, 2.0 mmol), Boc-Phe (530 mg, 2.0 mmol), Boc-Val (435 mg, 2.0 mmol), Boc-Ala (378 mg, 2.0 mmol), Boc-Asp(OcHx) (630 mg, 2.0 mmol), Boc-Ser(Bzl) (590 mg, 2.0 mmol), and Boc-His(Tos) (819 mg, 2.0 mmol). The peptide resin was removed from the synthesizer and carried through protocol steps 1–8 and reacted with 0.6 mL acetic anhydride in 12 mL 6% DIPEA/methylene chloride for 20 minutes. The resin was washed with steps 10–14 and dried under vacuum to yield 1.3 g of peptide resin.

The peptide resin was treated with HF as in Example 11 to yield, after lyophilization, 155 mg of a white solid. This crude peptide was purified by preparative HPLC as in Example 5 except that a linear gradient of 20–40% was run. The main peak was cut by analytical HPLC analysis of collected fractions, pooled and lyophilized to yield 35.2 mg of a white, amorphous powder. This compound was homogeneous by HPLC and gave a correct amino acid analysis.

EXAMPLE 18

Ac-[Lys$^{12}$,Ala$^{15}$,Nle$^{17}$,Val$^{26}$,Thr$^{28}$]-VIP

A 0.25 g (0.05 mmol) portion of Boc-Thr(Bzl)-BHA resin from Example 2 was subjected to solid phase synthesis as in Example 5 except that Boc-Lys(2-Cl-Z) in the thirteenth cycle was replaced by Boc-Ala (95 mg, 0.5 mmol). The peptide-resin was deblocked to yield 128 mg of crude peptide. Purification by HPLC yielded 35.8 mg of a white, amorphous powder. The compound was homogeneous by HPLC and gave a correct amino acid analysis. FAB-MS: MH calc. 3238.7, found 3237.9.

EXAMPLE 19

Ac-[Lys$^{12}$,Ala$^{14}$,Nle$^{17}$,Val$^{26}$,Thr$^{28}$]-VIP

A 0.25 g (0.05 mmol) portion of Boc-Thr(Bzl)-BHA resin from Example 2 was subjected to solid phase synthesis as in Example 5 except that Boc-Arg(Tos) in the fourteenth cycle was replaced by Boc-Ala (95 mg, 0.5 mmol). The peptide-resin 368 mg) was deblocked to yield 112 mg of crude peptide. Purification by HPLC yielded 24.7 mg of a white, amorphous powder. The compound was homogeneous by HPLC and gave a correct amino acid analysis. FAB-MS: MH calc. 3210.7, found 3210.8.

EXAMPLE 20

Ac-[Lys$^{12}$,Ala$^{13}$,Nle$^{17}$,Val$^{26}$,Thr$^{28}$]-VIP

A 0.255 g (0.05 mmol) portion of Boc-Thr(Bzl)-BHA resin from Example 2 was subjected to solid phase synthesis as in Example 5 except that Boc-Leu in the fifteenth cycle was replaced by Boc-Ala (95 mg, 0.5 mmol). The peptide-resin (416 mg) was deblocked to yield 125 mg of crude peptide. Purification by HPLC yielded 24.2 mg of a white, amorphous powder. The compound was homogeneous by HPLC and gave a correct amino acid analysis. FAB-MS: MH calc. 3253.7, found 3253.6.

EXAMPLE 21

Ac-[Ala$^{12}$,Nle$^{17}$,Val$^{26}$,Thr$^{28}$]-VIP

A 0.254 g (0.05 mmol) portion of Boc-Thr(Bzl)-BHA resin from Example 2 was subjected to solid phase synthesis as in Example 5 except that Boc-Lys(2-Cl-Z) in the first cycle was replaced by Boc-Ala (95 mg, 0.5 mmol). The peptide-resin was deblocked to yield 128 mg of crude peptide. Purification by HPLC yielded 27.0 mg of a white, amorphous powder. The compound was homogeneous by HPLC and gave a correct amino acid analysis. FAB-MS: MH calc. 3238.7, found 3238.1.

EXAMPLE 22

Ac-[Ala$^{11}$,Lys$^{12}$,Nle$^{17}$,Val$^{26}$,Thr$^{28}$]-VIP

Benzhydrylamine copolystyrene-1% divinylbenzene cross-linked resin (25.0 g, 17.5 milliequiv, 200-400 ASTM mesh, Bachem) was swelled in 160 mL methylene chloride, filtered and washed using steps 7-8 of the protocol in Table 1. The resin was resuspended in 160 mL methylene chloride and to this was added Boc-Thr(Bzl) (16.2 g, 52.5 mmole) and dicyclohexylcarbodiimide (5.4 g, 26.2 mmol). This mixture was shaken for 6 hours at room temperature, filtered and the protocol 10-14 of Table 1 were performed. Kaiser ninhydrin analysis was negative. Unreacted amine groups were capped by treating the resin with 5 mL acetic anhydride and 5 mL DIPEA in 150 mL methylene chloride for 60 minutes, filtered and washed with protocol steps 13-14. The resin was dried under vacuum overnight to yield 29.6 g of Boc-Thr(Bzl)-BHA resin. A portion of this resin was subjected to amino acid analysis which indicated a loading of 0.21 mmol Thr/g.

A 14.0 g (2.94 mmol) portion of this resin was subjected to solid phase synthesis using the above protocol as in Example 15. Eleven coupling cycles were performed of one cycle each with Boc-Leu (5.9 g, 23.5 mmol), Boc-Val (5.1 g, 23.5 mmol), Boc-Ser(Bzl) (6.9 g, 23.5 mmol), Boc-Asn (3.0 g, 13.0 mmol), Boc-Leu (5.9 g, 23.5 mmol) Boc-Tyr(2,6-DCB) (10.3 g, 23.5 mmol), Boc-Lys(2-Cl-Z) (9.8 g, 23.5 mmol), Boc-Lys(2-Cl-Z) (9.8 g, 23.5 mmol), Boc-Val (5.1 g, 23.5 mmol), Boc-Ala (4.4 g, 23.5 mmol), and Boc-Nle (5.4 g, 23.5 mmol) to give 26 g of Boc-decapeptide resin.

A 17.3 g (1.96 mmol) portion of this resin was coupled with four cycles of one cycle each with Boc-Gln (2.12 g, 8.6 mmol), Boc-Lys(2-Cl-Z) (6.5 g, 15.7 mmol), Boc-Arg(Tos) (6.7 g, 15.7 mmol), and Boc-Leu (3.9 g, 15.7 mmol). The resin was dried under vacuum to give 19.7 g of Boc-hexadecapeptide resin.

A 1.0 g (0.1 mmol) portion of this resin was carried through twelve coupling cycles of one cycle each with Boc-Lys(2-Cl-Z) (332 mg, 0.8 mmol), Boc-Ala (152 mg, 0.8 mmol), Boc-Tyr(2,6-DCB) (352 mg, 0.8 mmol), Boc-Asn (102 mg, 0.44 mmol), Boc-Asp(OcHx) (252 mg, 0.8 mmol), Boc-Thr(Bzl) (247 mg, 0.8 mmol), Boc-Phe (212 mg, 0.8 mmol), Boc-Val (173 mg, 0.8 mmol), Boc-Ala (152 mg, 0.8 mmol), Boc-Asp(OcHx) (252 mg, 0.8 mmol), Boc-Ser(Bzl) (236 mg, 0.8 mmol), and Boc-His(Tos) (328 mg, 0.8 mmol). The peptide resin was carried through protocol steps 1-8 and treated with 0.5 mL acetic anhydride in 15 mL 6% DIPEA/methylene chloride for 30 minutes. The resin was washed using steps 10-14 and dried under vacuum to yield 1.2 g.

The peptide resin was treated with HF as in Example 11 to yield, after lyophilization, 600 mg of a white solid. A 400 mg portion of this crude peptide was purified by Preparative HPLC as in Example 11. The main peak was cut by analytical HPLC analysis of collected fractions, pooled and lyophilized to yield 63 mg of a white, amorphous powder. This compound was homogeneous by HPLC and gave a correct amino acid analysis.

EXAMPLE 23

Ac-[Ala$^{10}$,Lys$^{12}$,Nle$^{17}$,Val$^{26}$,Thr$^{28}$]-VIP

A 1.0 g (0.1 mmol) portion of the Boc-hexadecapeptide resin from Example 22 was carried through twelve coupling cycles of one cycle each with Boc-Lys(2-Cl-Z) (332 mg, 0.8 mmol), Boc-Thr(Bzl) (247 mg, 0.8 mmol), Boc-Ala (152 mg, 0.8 mmol), Boc-Asn (102 mg, 0.44 mmol), Boc-Asp(OcHx) (252 mg, 0.8 mmol), Boc-Thr(Bzl) (247 mg, 0.8 mmol), Boc-Phe (212 mg, 0.8 mmol), Boc-Val (173 mg, 0.8 mmol), Boc-Ala (152 mg, 0.8 mmol), Boc-Asp(OcHx) (252 mg, 0.8 mmol), Boc-Ser(Bzl) (236 mg, 0.8 mmol), and Boc-His(Tos) (328 mg, 0.8 mmol). The peptide resin was carried through protocol steps 1-8 and treated with 0.5 mL acetic anhydride in 15 mL 6% DIPEA/methylene chloride for 30 minutes. The resin was washed using steps 10-14 and dried under vacuum to yield 1.1 g.

The peptide resin was treated with HF as in Example 11 to yield, after lyophilization, 700 mg of a white solid. A 290 mg portion of this crude peptide was purified by preparative HPLC as in Example 11 except that a linear gradient of 20-40% was run. The main peak was cut by analytical HPLC analysis of collected fractions, pooled and lyophilized to yield 35.7 mg of a white, amorphous powder. This compound was homogeneous by HPLC and gave a correct amino acid analysis.

EXAMPLE 24

Ac-[Ala$^9$,Lys$^{12}$,Nle$^{17}$,Val$^{26}$,Thr$^{28}$]-VIP

A 0.68 g (0.075 mmol) portion of the Boc-decapeptide resin from Example 17 was subjected to solid phase synthesis as in Example 15. Sixteen coupling cycles of one cycle each with Boc-Gln (102 mg, 0.41 mmol), Boc-Lys(2-Cl-Z) (314 mg, 0.75 mmol), Boc-Arg(Tos) (324 mg, 0.75 mmol), Boc-Leu (188 mg, 0.75 mmol), Boc-Lys(2-Cl-Z) (314 mg, 0.75 mmol), Boc-Thr(Bzl) (234 mg, 0.75 mmol), Boc-Tyr(2,6-DCB) (333 mg, 0.75 mmol), Boc-Ala (143 mg, 0.75 mmol), Boc-Asp(OcHx) (238 mg, 0.75 mmol), Boc-Thr(Bzl) (234 mg, 0.75 mmol), Boc-Phe (200 mg, 0.75 mmol), Boc-Val (164 mg, 0.75 mmol), Boc-Ala (143 mg, 0.75 mmol), Boc-Asp(OcHx) (238 mg, 0.75 mmol), Boc-Ser(Bzl) (223 mg, 0.75 mmol), and Boc-His(Tos) (310 mg, 0.75 mmol). The peptide resin was carried through protocol steps 1-8 and treated with 1.0 mL acetic anhydride in 15 mL 6% DIPEA/methylene chloride for 30 minutes. The resin was washed using steps 10-14 and dried under vacuum to yield 0.9 g. The peptide resin was treated with HF as in Example 11 to yield, after lyophilization, 336 mg of a white solid. This crude peptide was purified by preparative HPLC as in Example 11 except that a linear gradient of 10-40% in 2 hours at 4.0 ml/min was run. The main peak was cut by analytical HPLC analysis of collected fractions, pooled and lyophilized to yield 11.8 mg of a white, amorphous powder. This compound was homogeneous by HPLC and gave a correct amino acid analysis.

EXAMPLE 25

Ac-[Ala$^8$,Lys$^{12}$,Nle$^{17}$,Val$^{26}$,Thr$^{28}$]-VIP

A 2.0 g (0.2 mmol) portion of the Boc-hexadecapeptide resin from Example 22 was carried through four coupling cycles of one cycle each with Boc-Lys(2-Cl-Z) (664 mg, 1.6 mmol), Boc-Thr(Bzl) (495 mg, 1.6 mmol), Boc-Tyr(2,6-DCB) (705 mg, 1.6 mmol), and Boc-Asn (204 mg, 0.88 mmol) to give 2.2 g of Boc-eicosapeptide.

A 1.1 g (0.1 mmol) portion of this peptide resin was carried through eight coupling cycles of one cycle each with Boc-Ala (151 mg, 0.8 mmol), Boc-Thr(Bzl) (248 mg, 0.8 mmol), Boc-Phe (212 mg, 0.8 mmol), Boc-Val (174 mg, 0.8 mmol), Boc-Ala (151 mg, 0.8 mmol), Boc-Asp(OcHx) (252 mg, 0.8 mmol), Boc-Ser(Bzl) (236 mg, 0.8 mmol), and Boc-His(Tos) (328 mg, 0.8 mmol). The peptide resin was carried through protocol steps 1-8 and treated with 0.5 mL acetic anhydride in 15 mL 6% DIPEA/methylene chloride for 30 minutes. The resin was washed using steps 10-14 and dried under vacuum to yield 1.1 g.

The peptide resin was treated with HF as in Example 11 to yield, after lyophilization, 573 mg of a white solid. This crude peptide was purified by preparative HPLC as in Example 11 except that a linear gradient of 10-40% was run. The main peak was cut by analytical HPLC analysis of collected fractions, pooled and lyophilized to yield 69.0 mg of a white, amorphous powder. This compound was homogeneous by HPLC and gave a correct amino acid analysis.

EXAMPLE 26

Ac-[Ala$^7$,Lys$^{12}$,Nle$^{17}$,Val$^{26}$,Thr$^{28}$]-VIP

A 1.1 g (0.1 mmol) portion of the Boc-eicosapeptide resin from Example 25 was carried through eight coupling cycles of one cycle each with Boc-Asp(OcHx) (252 mg, 0.8 mmol), Boc-Ala (151 mg, 0.8 mmol), Boc-Phe (212 mg, 0.8 mmol), Boc-Val (174 mg, 0.8 mmol), Boc-Ala (151 mg, 0.8 mmol), Boc-Asp(OcHx) (252 mg, 0.8 mmol), Boc-Ser(Bzl) (236 mg, 0.8 mmol), and Boc-His(Tos) (328 mg, 0.8 mmol). The peptide resin was carried through protocol steps 1-8 and treated with 0.5 mL acetic anhydride in 15 mL 6% DIPEA/methylene chloride for 30 minutes. The resin was washed using steps 10-14 and dried under vacuum to yield 1.1 g.

The peptide resin was treated with HF as in Example 11 to yield, after lyophilization, 700 mg of a white solid. A portion of this crude peptide (400 mg) was purified by preparative HPLC as in Example 11 except that a linear gradient of 10-45% was run. The main peak was cut by analytical HPLC analysis of collected fractions, pooled and lyophilized to yield 29 mg of a white, amorphous powder. This compound was homogeneous by HPLC and gave a correct amino acid analysis.

EXAMPLE 27

Ac-[Ala$^6$,Lys$^{12}$,Nle$^{17}$,Val$^{26}$,Thr$^{28}$]-VIP

A 1.0 g (0.1 mmol) portion of the Boc-hexadecapeptide resin from Example 22 was carried through twelve coupling cycles of one cycle each with Boc-Lys(2-Cl-Z) (332 mg, 0.8 mmol), Boc-Thr(Bzl) (247 mg, 0.8 mmol), Boc-Tyr(2,6-DCB) (352 mg, 0.8 mmol), Boc-Asn (102 mg, 0.44 mmol), Boc-Asp(OcHx) (252 mg, 0.8 mmol), Boc-Thr(Bzl) (247 mg, 0.8 mmol), Boc-Ala (152 mg, 0.8 mmol), Boc-Val (173 mg, 0.8 mmol), Boc-Ala (152 mg, 0.8 mmol), Boc-Asp(OcHx) (252 mg, 0.8 mmol), Boc-Ser(Bzl) (236 mg, 0.8 mmol), and Boc-His(Tos) (328 mg, 0.8 mmol). The peptide resin was carried through protocol steps 1-8 and treated with 0.5 mL acetic anhydride in 15 mL 6% DIPEA/methylene chloride for 30 minutes. The resin was washed using steps 10-14 and dried under vacuum to yield 1.3 g.

The peptide resin was treated with HF as in Example 11 to yield, after lyophilization, 531.4 mg of a white solid. This crude peptide was purified by preparative HPLC as in Example 11. The main peak was cut by analytical HPLC analysis of collected fractions, pooled and lyophilized to yield 200 mg of a semipurified material. This compound was further purified by gel filtration on Sephadex G-25 in 10% AcOH to yield 104.5 mg of a white powder that was repurified by HPLC to yield 20 mg of a white, amorphous powder. This compound was homogeneous by HPLC and gave a correct amino acid analysis.

EXAMPLE 28

Ac-[Ala$^5$,Lys$^{12}$,Nle$^{17}$,Val$^{26}$,Thr$^{28}$]-VIP

A 3.0 g (0.3 mmol) portion of the Boc-hexadecapeptide resin from Example 22 was carried through seven coupling cycles of one cycle each with Boc-Lys(2-Cl-Z) (996 mg, 2.4 mmol), Boc-Thr(Bzl) (742 mg, 2.4 mmol), Boc-Tyr(2,6-DCB) (1.05 g, 2.4 mmol), Boc-Asn (302 mg, 1.3 mmol), Boc-Asp(OcHx) (757 mg, 2.4 mmol), Boc-Thr(Bzl) (742 mg, 2.4 mmol), and Boc-Phe (637 mg, 2.4 mmol) to give 3.6 g of Boc-tricosapeptide resin.

A 1.2 g (0.1 mmol) portion of this resin was carried through five cycles of one cycle each with Boc-Ala (151 mg, 0.8 mmol), Boc-Ala (151 mg, 0.8 mmol), Boc-Asp(OcHx) (252 mg, 0.8 mmol), Boc-Ser(Bzl) (236 mg, 0.8 mmol), and Boc-His(Tos) (328 mg, 0.8 mmol). The peptide resin was carried through protocol steps 1-8 and treated with 0.5 mL acetic anhydride in 15 mL 6% DIPEA/methylene chloride for 30 minutes. The resin was washed using steps 10-14 and dried under vacuum to yield 1.13 g.

The peptide resin was treated with HF as in Example 11 to yield, after lyophilization, 600 mg of a white solid. This crude peptide was purified by preparative HPLC as in Example 11 except that a linear gradient of 10-40% was run. The main peak was cut by analytical HPLC analysis of collected fractions, pooled and lyophilized to yield 64 mg of a white, amorphous powder. This compound was homogeneous by HPLC and gave a correct amino acid analysis.

EXAMPLE 29

Ac-[Ala$^3$,Lys$^{12}$,Nle$^{17}$,Val$^{26}$,Thr$^{28}$]-VIP

A 1.2 g (0.1 mmol) portion of the Boc-tricosapeptide resin from Example 28 was carried through five cycles of one cycle each with Boc-Val (174 mg, 0.8 mmol), Boc-Ala (151 mg, 0.8 mmol), Boc-Ala (151 mg, 0.8 mmol), Boc-Ser(Bzl) (236 mg, 0.8 mmol), and Boc-His(Tos) (328 mg, 0.8 mmol). The peptide resin was carried through protocol steps 1-8 and treated with 0.5 mL acetic anhydride in 15 mL 6% DIPEA/methylene chloride for 30 minutes. The resin was washed using steps 10-14 and dried under vacuum to yield 1.2 g.

The peptide resin was treated with HF as in Example 11 to yield, after lyophilization, 700 mg of a white solid. This crude peptide was purified twice by preparative HPLC as in Example 11 except that linear gradient of 10-45% and 20-45% were run. The main peak was cut by analytical HPLC analysis of collected fractions, pooled and lyophilized to yield 9.6 mg of a white, amorphous powder. This compound was homogeneous by HPLC and gave a correct amino acid analysis.

EXAMPLE 30

Ac-[Ala$^2$,Lys$^{12}$,Nle$^{17}$,Val$^{26}$,Thr$^{28}$]-VIP

A 0.25g (0.05 mmol) portion of Boc-Thr(Bzl)-BHA resin from Example 2 was subjected to solid phase synthesis as in Example 5 except that Boc-Ser(Bzl) in the twenty-sixth cycle was replaced by Boc-Ala (95 mg, 0.5 mmol). The peptide-resin (381 mg) was deblocked to yield 112 mg of crude peptide. Purification by HPLC yielded 41.2 mg of a white, amorphous powder. The compound was homogeneous by HPLC and gave a correct amino acid analysis. FAB-MS: MH calc. 3279.8, found 3279.5.

EXAMPLE 31

Ac-[Ala$^1$,Lys$^{12}$,Nle$^{17}$,Val$^{26}$,Thr$^{28}$]-VIP

A 1.2 g (0.1 mmol) portion of the Boc-tricosapeptide resin from Example 28 was carried through five cycles of one cycle each with Boc-Val (174 mg, 0.8 mmol), Boc-Ala (151 mg, 0.8 mmol), Boc-Asp(OcHx) (252 mg, 0.8 mmol), Boc-Ser(Bzl) (236 mg, 0.8 mmol), and Boc-Ala (151 mg, 0.8 mmol). The peptide resin was carried through protocol steps 1-8 and treated with 0.5 mL acetic anhydride in 15 mL 6% DIPEA/methylene chloride for 30 minutes. The resin was washed using steps 10-14 and dried under vacuum to yield 1 g.

The peptide resin was treated with HF as in Example 11 to yield, after lyophilization, 640 mg of a white solid. This crude peptide was purified twice by preparative HPLC as in Example 11 except that linear gradient of 20-50% and 25-40% were run. The main peaks were cut by analytical HPLC analysis of collected fractions, pooled and lyophilized to yield 45 mg of a white, amorphous powder. This compound was homogeneous by HPLC and gave a correct amino acid analysis. FAB-MS: calc. 3229.7, found 3228.8.

EXAMPLE 32

Ac-[Gly$^1$,Lys$^{12}$,Nle$^{17}$,Val$^{26}$,Thr$^{28}$]-VIP

A 4.0 g (0.4 mmol) portion of the Boc-hexadecapeptide resin from Example 22 was carried through ten coupling cycles of one cycle each with Boc-Lys(2-Cl-Z) (1.33 g, 3.2 mmol), Boc-Thr(Bzl) (990 mg, 3.2 mmol), Boc-Tyr(2,6-DCB) (1.41 g, 3.2 mmol), Boc-Asn (409 mg, 1.76 mmol), Boc-Asp(OcHx) (1.02 g, 3.2 mmol), Boc-Thr(Bzl) (990 mg, 3.2 mmol), Boc-Phe (849 mg, 3.2 mmol), Boc-Val (695 mg, 3.2 mmol), Boc-Ala (606 mg, 3.2 mmol), and Boc-Asp(OcHx) (1.02 mg, 3 2 mmol) to give 6.0 g of Boc-hexacosapeptide resin.

A 0.629 g (0.08 mmol) portion of this resin was carried through two cycles of one cycle each with Boc-Ser(Bzl) (118 mg, 0.4 mmol), and Boc-Gly (70 mg, 0.4 mmol). The peptide was carried through protocol steps 1-8 and treated with 0.5 mL acetic anhydride in 15 mL 6% DIPEA/methylene chloride for 30 minutes. The resin was washed using steps 10-14 and dried under vacuum to yield 546 mg.

The peptide resin was treated with HF as in Example 11 to yield, after lyophilization, 210 mg of a white solid. This crude peptide was purified by preparative HPLC as in Example 5. The main peak was cut by analytical HPLC analysis of collected fractions, pooled and lyophilized to yield 24.0 mg of a white, amorphous powder. This compound was homogeneous by HPLC and gave a correct amino acid analysis. FAB-MS: calc. 3215.7, found 3215.4.

EXAMPLE 33

Ac-[Leu$^5$,Lys$^{12}$,Nle$^{17}$,Val$^{26}$,Thr$^{28}$]-VIP

A 1.0 g (0.1 mmol) portion of the Boc-hexadecapeptide resin from Example 22 was carried through twelve coupling cycles of one cycle each with Boc-Lys(2-Cl-Z) (332 mg, 0.8 mmol), Boc-Thr(Bzl) (247 mg, 0.8 mmol), Boc-Tyr(2,6-DCB) (352 mg, 0.8 mmol), Boc-Asn (102 mg, 0.44 mmol), Boc-Asp(OcHx) (252 mg, 0.8 mmol), Boc-Thr(Bzl) (247 mg, 0.8 mmol), Boc-Phe (212 mg, 0.8 mmol), Boc-Leu (199 mg, 0.8 mmol), Boc-Ala (152 mg, 0.8 mmol), Boc-Asp(OcHx) (252 mg, 0.8 mmol), Boc-Ser(Bzl) (236 mg, 0.8 mmol), and Boc-His(-Tos) (328 mg, 0.8 mmol). The peptide resin was carried through protocol steps 1-8 and treated with 0.5 mL acetic anhydride in 15 mL 6% DIPEA/methylene chloride for 30 minutes. The resin was washed using steps 10-14 and dried under vacuum to yield 0.8 g.

The peptide resin was treated with HF as in Example 11 to yield, after lyophilization, 238 mg of a white solid. This crude peptide was purified twice by preparative HPLC as in Example 11. The main peaks were cut by analytical HPLC analysis of collected fractions, pooled and lyophilized to yield 17.4 mg of a white, amorphous powder. This compound was homogeneous by HPLC and gave a correct amino acid analysis.

EXAMPLE 34

Boc-3-(1'-Naphthyl)-alanine (Boc-1-Nal)

1.0 g (4.6 mmol) of 3-(1'-naphthyl)-alanine and 512 mg (4.8 mmol) of sodium carbonate were dissolved in 20 mL H$_2$O and 20 mL dioxane. 1.26 g (5.77 mmol) of di-tert-butyldicarbonate in 5 ml dioxane was slowly added. The mixture was stirred overnight at room temperature. Most of the dioxane was evaporated under vacuum and the residue was taken up in 35 mL H$_2$O. This solution was washed with 3×25 mL Et$_2$O, acidified with 10% citric acid/H$_2$O to pH 2 and extracted with 4×50 mL methylene chloride. The combined methylene chloride layers were dried over MgSO$_4$, filtered, and concentrated under vacuum to an oily foam. This material was recrystallized from EtOAc/petroleum ether at −20° C. to yield 1.35 g (93%) of white crystals. mp 144°-146° C. [a]$_D$—47.8° (c 1, EtOH). $^1$H NMR compatible with structure.

EXAMPLE 35

Ac-[1-Nal$^6$,Lys$^{12}$,Nle$^{17}$,Val$^{26}$,Thr$^{28}$]-VIP

Benzhydrylamine copolystyrene-1% divinylbenzene cross-linked resin (30 g, 21.4 mequiv, 200-400 ASTM mesh, Bachem) was treated as in Example 22 except that 19.9 g Boc-Thr(Bzl) (64.3 mmole) and 6.6 g dicyclohexylcarbodiimide (32.1 mmol) were used. This mixture was shaken for 18 hours at room temperature, filtered and then protocol steps 10-14 of Table 1 were performed. Kaiser ninhydrin analysis was negative. Unreacted amine groups were capped by treating the resin with 8 mL acetic anhydride and 8 mL DIPEA in 200 mL methylene chloride for 60 minutes, filtered and washed with protocol steps 13-14. The resin was dried under vacuum overnight to yield 34.2 g of Boc-Thr(Bzl)-BHA resin. A portion of this resin was subjected to amino acid analysis which indicated a loading of 0.47 mmol Thr/g.

A 0.75 g (0.35 mmol) portion of this Boc-Thr(Bzl)-BHA resin was subjected to solid phase synthesis on an Applied Biosystems model 430A peptide synthesizer as in Example 11. Twenty-one coupling cycles were performed of one cycle each with Boc-Leu (499 mg, 2.0 mmol), Boc-Val (435 mg, 2.0 mmol), Boc-Ser(Bzl) (590 mg, 2.0 mmol), Boc-Asn (464 mg, 2.0 mmol), Boc-Leu (499 mg, 2.0 mmol), Boc-Tyr(2,6-DCB) (880 mg, 2.0 mmol), Boc-Lys(2-Cl-Z) (830 mg, 2.0 mmol), Boc-Lys(2-Cl-Z) (830 mg, 2.0 mmol), Boc-Val (435 mg, 2.0 mmol), Boc-Ala (378 mg, 2.0 mmol), Boc-Nle (462 mg, 2.0 mmol), Boc-Gln (492 mg, 2.0 mmol), Boc-Lys(2-Cl-Z) (830 mg, 2.0 mmol), Boc-Arg(Tos) (856 mg, 2.0 mmol), Boc-Leu (499 mg, 2.0 mmol), Boc-Lys(2-Cl-Z) (830 mg, 2.0 mmol), Boc-Thr(Bzl) (618 mg, 2.0 mmol), Boc-Tyr(2,6-DCB) (880 mg, 2.0 mmol), Boc-Asn (464 mg, 2.0 mmol), Boc-Asp(OcHx) (630 mg, 2.0 mmol), and Boc-Thr(Bzl) (618 mg, 2.0 mmol) to give 2.59 g of Boc-docosapeptide resin.

A 0.74 g (0.1 mmol) portion of this resin was subjected to solid phase synthesis as in Example 15. Six cycles were performed of one cycle each with Boc-1-Nal (126 mg, 0.4 mmol), Boc-Val (87 mg, 0.4 mmol), Boc-Ala (76 mg, 0.4 mmol), Boc-Asp(OcHx) (126 mg, 0.4 mmol), Boc-Ser(Bzl) (118 mg, 0.4 mmol), and Boc-His(Tos) (328 mg, 0.8 mmol). The peptide-resin was then carried through protocol steps 1–8 and reacted twice with 1.0 mL acetic anhydride and 15 mL 6% DIPEA/methylene chloride for 60 minutes. The resin was washed using steps 10–14 and dried under vacuum to yield 0.8 g. The peptide-resin was deblocked as in Example 5 to yield 366 mg of crude peptide. The peptide was purified by HPLC as in Example 5, except that a linear gradient of 27–37% was run, to yield 49.6 mg of a white, amorphous powder. The compound was homogeneous by HPLC and gave a correct amino acid analysis. FAB-MS: MH calc. 3345.9, found 3345.5.

EXAMPLE 36

Boc-p-Fluoro-Phenylalanine (Boc-p-F-Phe)

988 mg (4.91 mmol) of p-fluoro-phenylalanine·$H_2O$ and 525 mg (4.95 mmol) of sodium carbonate were dissolved in 30 mL of 50% dioxane/$H_2O$. 1.3 g (5.95 mmol) of di-tert-butyl-dicarbonate in 3 mL dioxane was slowly added. The mixture was stirred overnight at room temperature and then evaporated. The residue was dissolved in 20 mL $H_2O$, washed with 3×20 mL $Et_2O$, acidified to pH 2 with 0.1N HCl, and extracted with 3×30 mL EtOAc. The combined EtOAc layers were dried over $MgSO_4$, filtered, and concentrated to an oil. This material was crystallized from EtOAc/hexane to give 1.14 g (82%) of fine white needles. mp 52°–54° C. $[a]_D + 23.13°$ (c 1, EtOAc). $^1H$ NMR compatible with structure. Anal. calcd for $C_{14}H_{18}FNO_4$: C, 59.39; H, 6.40; N, 4.94. Found: C, 59.51; H, 6.60; N, 4.95.

EXAMPLE 37

Ac-[p-F-Phe$^6$,Lys$^{12}$,Nle$^{17}$,Val$^{26}$,Thr$^{28}$]-VIP

A 0.68 g (0.1 mmol) portion of the Boc-docosapeptide resin from Example 35 was subjected to solid phase synthesis as in Example 15. Six cycles were performed of one cycle each with Boc-p-F-Phe (113 mg, 0.4 mmol), Boc-Val (87 mg, 0.4 mmol), Boc-Ala (76 mg, 0.4 mmol), Boc-Asp(OcHx) (126 mg, 0.4 mmol), Boc-Ser(Bzl) (118 mg, 0.4 mmol), and Boc-His(Tos) (328 mg, 0.8 mmol). The peptide-resin was then carried through protocol steps 1–8 and reacted twice with 1.0 ml acetic anhydride and 15 mL 6% DIPEA/methylene chloride for 60 minutes. The resin was washed using steps 10–14 and dried under vacuum to yield 0.7 g. The peptide-resin was deblocked as in Example 5 to yield 270 mg of crude peptide. The peptide was purified by HPLC as in Example 5 to yield 84.1 mg of a white, amorphous powder. The compound was homogeneous by HPLC and gave a correct amino acid analysis. FAB-MS: MH calc. 3313.8, found 3313.0.

EXAMPLE 38

Ac-[Glu$^8$,Lys$^{12}$,Nle$^{17}$,Val$^{26}$,Thr$^{28}$]-VIP

A 7.48 g (1.0 mmol) portion of the Boc-hexapeptide resin from Example 15 was carried through ten coupling cycles of one cycle each with Boc-Tyr(2,6-DCB) (1.76 g, 4.0 mmol), Boc-Lys(2-Cl-Z) (1.66 g, 4.0 mmol), Boc-Lys(2-Cl-Z) (1.66 g, 4.0 mmol), Boc-Val (869 mg, 4.0 mmol), Boc-Ala (1.5 g, 8.0 mmol), Boc-Nle (925 mg, 4.0 mmol), Boc-Gln (1.08 g, 4.4 mmol), Boc-Lys(2-Cl-Z) (1.66 g, 4.0 mmol), Boc-Arg(Tos) (1.71 g, 4.0 mmol), and Boc-Leu (998 mg, 4.0 mmol). The peptide resin was dried under vacuum to give 9.6 g of Boc-hexadecapeptide resin.

A 7.68 g (0.8 mmol) portion of this resin was carried through one coupling cycle with Boc-Lys(Fmoc) (1.5 g, 3.2 mmol) to give 8.32 g of Boc-heptadecapeptide resin.

A 6.24 g (0.6 mmol) portion of this resin was carried through two coupling cycles of one cycle each with Boc-Thr(Bzl) (742 mg, 2.4 mmol) and Boc-Tyr(2,6-DCB) (1.06 g, 2.4 mmol) to give 6.28 g of Boc-nonadecapeptide resin.

A 2.09 g (0.2 mmol) portion of this resin was carried through nine coupling cycles of one cycle each with Boc-Asn (204 mg, 0.88 mmol), Boc-Glu(OFm) (340 mg, 0.8 mmol), Boc-Thr(Bzl) (248 mg, 0.8 mmol), Boc-Phe (212 mg, 0.8 mmol), Boc-Val (174 mg, 0.8 mmol), Boc-Ala (151 mg, 0.8 mmol), Boc-Asp(OcHx) (258 mg, 0.8 mmol), Boc-Ser(Bzl) (236 mg, 0.8 mmol), and Boc-His(Bom) (330 mg, 0.88 mmol). The peptide resin was carried through protocol steps 1–8 and treated with 0.25 mL acetic anhydride and 70 mL DIPEA in 20 mL methylene chloride for 20 minutes. This resin was treated with 20% piperidine/DMF for 20 minutes, washed using steps 10–14 and dried under vacuum to yield 2.28 g.

A 0.57 g (0.05 mmol) portion of this resin was treated as in Example 11 with 6 mL dimethylsulfide and 2 mL liquid HF for 2 hours and 0° C. The reaction mixture was evaporated and the residue was treated with 1.0 mL anisole and 9 mL liquid HF for 45 minutes at 0° C. The reaction mixture was evaporated and the residue was washed with 1×15 mL $Et_2O$ and 3×15 mL EtOAc. The resin was extracted with 3×15 mL 10% AcOH. The combined aqueous filtrates were lyophilized to yield 250 mg of a white solid.

This crude material was purified by preparative HPLC as in Example 5 except that a linear gradient of 10–40% in 4 hours was run. The main peak was cut by analytical HPLC analysis of collected fractions, pooled and lyophilized to yield 40.0 mg of a white, amorphous powder. This compound was homogeneous by HPLC and gave a correct amino acid analysis.

EXAMPLE 39

Boc-3-(2'-Naphthyl)-alanine (Boc-2-Nal)

1.05 g (4.83 mmol) of 3-(2'-naphthyl)-alanine and 510 mg (4.83 mmol) of sodium carbonate were treated with 1.26 g (5 77 mmol) di-tert-butyl-dicarbonate as in Example 34. After workup, the methylene chloride layers were evaporated to a clear oil that was crystallized from EtOAc/petroleum ether to yield 1.25 g (82%) of white needles. mp 92°–94° C. $[\alpha]_D$+43.15? (c 1, EtOH). $^1$H NMR compatible with structure. Anal. calcd for $C_{18}H_{21}NO_4$: C, 68.56; H, 6.71; N, 4.44. Found: C, 68.66; H, 7.02; N, 4.31.

EXAMPLE 40

Ac-[2-Nal$^{10}$,Lys$^{12}$,Nle$^{17}$,Val$^{26}$,Thr$^{28}$]-VIP

A 0.85 g (0.4 mmol) portion of the Boc-Thr(Bzl)-BHA resin from Example 35 was subjected to solid phase synthesis on an Applied Biosystems model 430A peptide synthesizer as in Example 11. Seventeen coupling cycles were performed of one cycle each with Boc-Leu (499 mg, 2.0 mmol), Boc-Val (435 mg, 2.0 mmol), Boc-Ser(Bzl) (590 mg, 2.0 mmol), Boc-Asn (464 mg, 2.0 mmol), Boc-Leu (499 mg, 2.0 mmol), Boc-Tyr(2,6-DCB) (880 mg, 2.0 mmol), Boc-Lys(2-Cl-Z) (830 mg, 2.0 mmol), Boc-Lys(2-Cl-Z) (830 mg, 2.0 mmol), Boc-Val (435 mg, 2.0 mmol), Boc-Ala (378 mg, 2.0 mmol), Boc-Nle (462 mg, 2.0 mmol), Boc-Gln (492 mg, 2.0 mmol), Boc-Lys(2-Cl-Z) (830 mg, 2.0 mmol), Boc-Arg(Tos) (856 mg, 2.0 mmol), Boc-Leu (499 mg, 2.0 mmol), Boc-Lys(2-Cl-Z) (830 mg, 2.0 mmol), and Boc-Thr(Bzl) (618 mg, 2.0 mmol) to give 2.8 g of Boc-octadecapeptide resin.

A 0.7 g (0.1 mmol) portion of this resin was carried through ten cycles of one cycle each with Boc-2-Nal (252 mg, 0.8 mmol), Boc-Asn (102 mg, 0.44 mmol), Boc-Asp(OcHx) (252 mg, 0.8 mmol), Boc-Thr(Bzl) (247 mg, 0.8 mmol), Boc-Phe (212 mg, 0.8 mmol), Boc-Val (174 mg, 0.8 mmol), Boc-Ala (151 mg, 0.8 mmol), Boc-Asp(OcHx) (252 mg, 0.8 mmol), Boc-Ser(Bzl) (236 mg, 0.8 mmol), and Boc-His(Tos) (328 mg, 0.8 mmol). The peptide resin was carried through protocol steps 1–8 and treated with 1.0 mL acetic anhydride in 15 mL 6% DIPEA/methylene chloride for 30 minutes. The resin was washed using steps 10–14 and dried under vacuum to yield 0.9 g. The peptide-resin was deblocked as in Example 5 to yield 210 mg of crude peptide. The peptide was purified by HPLC as in Example 5 to yield 46.8 mg of a white, amorphous powder. The compound was homogeneous by HPLC and gave a correct amino acid analysis. FAB-MS: MH calc. 3329.8, found 3328.8.

EXAMPLE 41

Ac-[p-NH$_2$-Phe$^{10}$,Lys$^{12}$,Nle$^{17}$,Val$^{26}$,Thr$^{28}$]-VIP

A 0.7 g (0.1 mmol) portion of the Boc-octadecapeptide resin from Example 40 was carried through ten cycles of one cycle each with Boc-p-NH(Z)-Phe (331 mg, 0.8 mmol), Boc-Asn (102 mg, 0.44 mmol), Boc-Asp(OcHx) (252 mg, 0.8 mmol), Boc-Thr(Bzl) (247 mg, 0.8 mmol), Boc-Phe (212 mg, 0.8 mmol), Boc-Val (174 mg, 0.8 mmol), Boc-Ala (151 mg, 0.8 mmol), Boc-Asp(OcHx) (252 mg, 0.8 mmol), Boc-Ser(Bzl) (236 mg, 0.8 mmol), and Boc-His(Tos) (328 mg, 0.8 mmol). The peptide resin was carried through protocol steps 1–8 and treated with 1.0 mL acetic anhydride in 15 mL 6% DIPEA/methylene chloride for 30 minutes. The resin was washed using steps 10–14 and dried under vacuum to yield 0.9 g. The peptide-resin was deblocked as in Example 5 to yield 247 mg of crude peptide. The peptide was purified by HPLC as in Example 5 to yield 32.7 mg of a white, amorphous powder. The compound was homogeneous by HPLC and gave a correct amino acid analysis. FAB-MS: MH calc. 3294.8, found 3294.1.

EXAMPLE 42

Boc-O-Methyl-Tyrosine (Boc-O-Me-Tyr)

1.0 g (5.1 mmol) of O-methyl-tyrosine and 1.08 g (10.2 mmol) of sodium carbonate were treated with 1.7 g (7.7 mmol) di-tert-butyl-dicarbonate as in Example 34 except that 25 mL H$_2$O and 12 mL dioxane were used. After workup, the methylene chloride layers were evaporated to a clear oil that was crystallized from Et$_2$O/ Petroleum ether to yield 1.1 g (73%) of white solid. mp 94°–96° C.

EXAMPLE 43

Ac-[O-Me-Tyr$^{10}$,Lys$^{12}$,Nle$^{17}$,Val$^{26}$,Thr$^{28}$]-VIP

A 0.85 g (0.4 mmol) portion of the Boc-Thr(Bzl)-BHA resin from Example 35 was subjected to solid phase synthesis on an Applied Biosystems model 430A peptide synthesizer as in Example 11. Thirteen coupling cycles were performed of one cycle each with Boc-Leu (499 mg, 2.0 mmol), Boc-Val (435 mg, 2.0 mmol), Boc-Ser(Bzl) (590 mg, 2.0 mmol), Boc-Asn (464 mg, 2.0 mmol), Boc-Leu (499 mg, 2.0 mmol), Boc-Tyr(2,6-DCB) (880 mg, 2.0 mmol), Boc-Lys(2-Cl-Z) (830 mg, 2.0 mmol), Boc-Lys(2-Cl-Z) (830 mg, 2.0 mmol), Boc-Val (435 mg, 2.0 mmol), Boc-Ala (378 mg, 2.0 mmol), Boc-Nle (462 mg, 2.0 mmol), Boc-Gln (492 mg, 2.0 mmol), and Boc-Lys(2-Cl-Z) (830 mg, 2.0 mmol) to give 1.9 g of Boc-tetradecapeptide resin.

This resin was carried through four coupling cycles as in Example 15 of one cycle each with Boc-Arg(Tos) (685 mg, 1.6 mmol), Boc-Leu (399 mg, 1.6 mmol), Boc-Lys(2-Cl-Z) (664 mg, 1.6 mmol) and Boc-Thr(Bzl) (495 mg, 1.6 mmol) to give 2.1 g of Boc-octadecapeptide resin.

A 0.5 g (0.1 mmol) portion of this resin was carried through one coupling cycle as in Example 15 with Boc-O-Me-Tyr (118 mg, 0.4 mmol) to give 0.5 g of Boc-nonadecapeptide resin.

This resin was carried through nine coupling cycles as in Example 5 of one cycle each with Boc-Asn (232 mg, 1.0 mmol), Boc-Asp(OcHx) (315 mg, 1.0 mmol), Boc-Thr(Bzl) (309 mg, 1.0 mmol), Boc-Phe (265 mg, 1.0 mmol), Boc-Val (217 mg, 1.0 mmol), Boc-Ala (189 mg, 1.0 mmol), Boc-Asp(OcHx) (315 mg, 1.0 mmol), Boc-Ser(Bzl) (295 mg, 1.0 mmol), and Boc-His(Tos) (409 mg, 1.0 mmol). The peptide resin was carried through protocol steps 1–8 and treated with 1.0 mL acetic anhydride in 15 mL 6% DIPEA/methylene chloride for 30 minutes. The resin was washed using steps 10–14 and dried under vacuum. The peptide-resin was deblocked as in Example 5 to yield 154 mg of crude peptide. The peptide was purified by HPLC as in Example 5 to yield 36.4 mg of a white, amorphous powder. The compound was homogeneous by HPLC and gave a correct amino acid analysis. FAB-MS: MH calc. 3309.8, found 3309.2.

EXAMPLE 44

Boc-m-Fluoro-DL-Tyrosine(Benzyl) (Boc-m-F-DL-Tyr(Bzl))

1.94 g (9.74 mmol) of m-fluoro-DL-tyrosine was dissolved in 10.1 mL 2N NaOH. 1.22 g (4.87 mmol) of CuSO$_4$.5H$_2$O in 5 mL H$_2$O was added. The mixture was heated to 50°–60° C. for 10 minutes and then cooled in ice. 42 mL of methanol were added with vigorous stirring. While stirring in an ice bath, 2.25 g (13.1 mmol) of benzyl bromide was added dropwise. After 30 minutes, the mixture was warmed to room temperature and let stir overnight. The steel-blue precipitate was filtered off and washed with 20 mL each of 20% H₂O/MeOH, MeOH, and acetone, and then dried under vacuum to give 3.14 g. This material was suspended in 100 mL 50% EtOH/H₂O and warmed to reflux. 3.62 g (9.7 mmol) Na₂.EDTA.H₂O was added and the solution was diluted with 150 mL 50% EtOH/H₂O. The solution was filtered hot and the filtrate was cooled for 48 hours. The off-white precipitate was filtered off and dried to give 3.57 g.

A 3.42 g (9.7 mmol) portion of the solid and 2.05 g (19.3 mmol) sodium carbonate were suspended in 75 mL H₂O and 25 mL dioxane. 3.2 g (14.6 mmol) of di-tert-butyldicarbonate in 3 mL dioxane was added and the mixture was stirred at room temperature overnight. Most of the dioxane was evaporated under vacuum and the residue taken up in 75 mL H₂O. The solution was washed with 3×25 mL Et₂O, acidified to pH 2 with 10% citric acid, and extracted with 3×40 mL methylene chloride. The combined methylene chloride layers were dried over MgSO₄, filtered, and concentrated to an oily foam. This material was crystallized from Et₂O/petroleum ether to yield 1.8 g (47%) of a white powder. mp 122°-122.5° C. ¹H NMR was compatible with structure.

EXAMPLE 45

Ac-[Lys$^{12}$,Nle$^{17}$,m-F-Tyr$^{22}$,Val$^{26}$,Thr$^{28}$]-VIP

A 0.4 g (0.1 mmol) portion of benzhydrylamine resin (100-200 ASTM mesh, Bachem) was subjected to solid phase synthesis using the above protocol as in Example 5. Twenty-eight coupling cycles were performed of one cycle each with Boc-Thr(Bzl) (309 mg, 1.0 mmol) Boc-Leu (249 mg, 1.0 mmol), Boc-Val (217 mg, 1.0 mmol), Boc-Ser(Bzl) (295 mg, 1.0 mmol), Boc-Asn (232 mg, 1.0 mmol), Boc-Leu (249 mg, 1.0 mmol), Boc-m-F-Tyr(Bzl) (195 mg, 0.5 mmol), Boc-Lys(2-Cl-Z) (415 mg, 1.0 mmol), Boc-Lys(2-Cl-Z) (415 mg, 1.0 mmol), Boc-Val (217 mg, 1.0 mmol), Boc-Ala (189 mg, 1.0 mmol), Boc-Nle (231 mg, 1.0 mmol), Boc-Gln (246 mg, 1.0 mmol), Boc-Lys(2-Cl-Z) (415 mg, 1.0 mmol), Boc-Arg(Tos) (428 mg, 1.0 mmol), Boc-Leu (249 mg, 1.0 mmol), Boc-Lys(2-Cl-Z) (415 mg, 1.0 mmol), Boc-Thr(Bzl) (309 mg, 1.0 mmol) Boc-Tyr(2,6-DCB) (440 mg, 1.0 mmol), Boc-Asn (232 mg, 1.0 mmol), Boc-Asp(OcHx) (315 mg, 1.0 mmol), Boc-Thr(Bzl) (309 mg, 1.0 mmol), Boc-Phe (265 mg, 1.0 mmol), Boc-Val (217 mg, 1.0 mmol), Boc-Ala (189 mg, 1.0 mmol), Boc-Asp(OcHx) (315 mg, 1.0 mmol), Boc-Ser(Bzl) (295 mg, 1.0 mmol), and Boc-His(Tos) (409 mg, 1.0 mmol). The peptide-resin was then carried through protocol steps 1-8 and treated with 0.5 ml acetic anhydride in 10 mL 6% DIPEA/methylene chloride for 60 minutes. The resin was washed using steps 10-14 and dried under vacuum to yield 639 mg.

The peptide-resin was deblocked as in Example 5 to yield 200 mg of crude peptide. Purification by HPLC, as in Example 5, yielded 25.6 mg of a white, amorphous powder. The compound was homogeneous by HPLC and gave a correct amino acid analysis. FAB-MS: MH calc. 3313.8, found 3313.7.

EXAMPLE 46

Ac-[Lys$^{12}$,Nle$^{17}$,Val$^{26}$,Thr$^{28}$,Gly$^{29,30}$,Met$^{31}$]-VIP

A 0.188 g (0.075 mmol) portion of benzhydrylamine resin (100-200 ASTM mesh, Advanced ChemTech) was subjected to solid phase synthesis using the above protocol as in Example 5. Thirty-one coupling cycles were performed of one cycle each with Boc-Met (187 mg, 0.75 mmol), Boc-Gly (131 mg, 0.75 mmol), Boc-Gly (131 mg, 0.75 mmol), Boc-Thr(Bzl) (232 mg, 0.75 mmol) Boc-Leu (187 mg, 0.75 mmol), Boc-Val (163 mg, 0.75 mmol), Boc-Ser(Bzl) (221 mg, 0.75 mmol), Boc-Asn (174 mg, 0.75 mmol), Boc-Leu (187 mg, 0.75 mmol), Boc-Tyr(2,6-DCB) (330 mg, 0.75 mmol), Boc-Lys(2-Cl-Z) (311 mg, 0.75 mmol), Boc-Lys(2-Cl-Z) (311 mg, 0.75 mmol), Boc-Val (163 mg, 0.75 mmol), Boc-Ala (142 mg, 0.75 mmol), Boc-Nle (173 mg, 0.75 mmol), Boc-Gln (185 mg, 0.75 mmol), Boc-Lys(2-Cl-Z) (311 mg, 0.75 mmol), Boc-Arg(Tos) (321 mg, 0.75 mmol), Boc-Leu (187 mg, 0.75 mmol), Boc-Lys(2-Cl-Z) (311 mg, 0.75 mmol), Boc-Thr(Bzl) (232 mg, 0.75 mmol), Boc-Tyr(2,6-DCB) (330 mg, 0.75 mmol), Boc-Asn (174 mg, 0.75 mmol), Boc-Asp(OcHx) (236 mg, 0.75 mmol), Boc-Thr(Bzl) (232 mg, 0.75 mmol), Boc-Phe (199 mg, 0.75 mmol), Boc-Val (163 mg, 0.75 mmol), Boc-Ala (142 mg, 0.75 mmol), Boc-Asp(OcHx) (236 mg, 0.75 mmol), Boc-Ser(Bzl) (221 mg, 0.75 mmol), and Boc-His(Tos) (307 mg, 0.75 mmol). The peptide-resin was then carried through protocol steps 1-8 and treated with 0.5 ml acetic anhydride in 10 mL 6% DIPEA/methylene chloride for 60 minutes. The resin was washed using steps 10-14 and dried under vacuum to yield 444 mg.

The peptide-resin was deblocked as in Example 5 to yield 177 mg of crude peptide. Purification by HPLC, as in Example 5, yielded 23.5 mg of a white, amorphous powder. The compound was homogeneous by HPLC and gave a correct amino acid analysis. FAB-MS: MH calc. 3541.1, found 3540.1.

EXAMPLE 47

Ac-[Lys$^{12}$,Nle$^{17}$,Val$^{26}$,Thr$^{28}$,Gly$^{29,30}$,Cys(Acm)$^{31}$]-VIP

Benzhydrylamine copolystyrene-1% divinylbenzene cross-linked resin (10.0 g, 7.0 mequiv, 200-400 ASTM mesh, Bachem) was derivatized as in Example 10 except that Boc-Cys(Acm) (3.4 g, 11.6 mmole), HOBT (2.1 g, 15.8 mmol), and dicyclohexylcarbodiimide (2.2 mg, 10.5 mmol) were used. This mixture was shaken for 8 hours at room temperature to give a negative Kaiser ninhydrin analysis. The resin was dried under vacuum overnight to yield 12 g of Boc-Cys(Acm)-BHA resin. A portion of this resin was subjected to amino acid analysis which indicated a loading of 0.44 mmol Cys/g.

A 1.0 g (0.44 mmol) portion of this resin was subjected to solid phase synthesis on a Biosearch model 9500 peptide synthesizer. All couplings were performed using five fold excesses of equal molar equivalents of Boc-amino acid and dicyclohexylcarbodiimide. Boc-asparagine and Boc-glutamine were coupled as the respective HOBT active esters. Thirty coupling cycles were performed of one cycle each with Boc-Gly (465 mg, 2.6 mmol), Boc-Gly (465 mg, 2.6 mmol), Boc-Thr(Bzl) (757 mg, 2.5 mmol), Boc-Leu (633 mg, 2.5 mmol), Boc-Val (532 mg, 2.5 mmol), Boc-Ser(Bzl) (780 mg, 2.6 mmol), Boc-Asn (580 mg, 2.5 mmol), Boc-Leu (633 mg, 2.5 mmol), Boc-Tyr(Bzl) (947 mg, 2.5 mmol), Boc-Lys(2-Cl-Z) (1.02 g, 2.5 mmol), Boc-Lys(2-Cl-Z) (1.02 g, 2.5 mmol), Boc-Val (532 mg, 2.5 mmol), Boc-Ala (500 mg, 2.6 mmol), Boc-Nle (680 mg, 2.9 mmol), Boc-Gln (650 mg, 2.6 mmol), Boc-Lys(2-Cl-Z) (1.02 g, 2.5 mmol), Boc-Arg(Tos) (1.13 g, 2.6 mmol), Boc-Leu (633 mg, 2.5 mmol), Boc-Lys(2-Cl-Z) (1.02 g, 2.5 mmol), Boc-Thr(Bzl) (757 mg, 2.5 mmol), Boc-Tyr(Bzl) (947 mg, 2.5 mmol), Boc-Asn (580 mg, 2.5 mmol), Boc-Asp(OcHx) (835 mg, 2.6 mmol), Boc-Thr(Bzl) (757 mg, 2.5 mmol), Boc-Phe (780 mg, 2.9 mmol), Boc-Val (532 mg, 2.5 mmol), Boc-Ala (500 mg, 2.6 mmol), Boc-Asp(OcHx) (835 mg, 2.6 mmol), Boc-Ser(Bzl) (780 mg, 2.6 mmol), and Boc-His(Tos) (1.08 g, 2.6 mmol). The peptide resin was deprotected and treated with acetic anhydride 30 minutes. The resin was dried under vacuum to yield 3.2 g of peptide resin.

A 1.5 g portion of this peptide resin was deblocked as in Example 11 to yield 525 mg of crude peptide. Purification by HPLC, as in Example 5, yielded 47 mg of a white, amorphous powder. The compound was homogeneous by HPLC and gave a correct amino acid analysis. FAB-MS: MH calc. 3583.1, found 3583.6.

EXAMPLE 48

Ac-[Lys$^{12}$,Nle$^{17}$,Val$^{26}$,Thr$^{28}$,Gly$^{29,30}$,Thr$^{31}$]-VIP

A 0.4 g (0.1 mmol) portion of benzhydrylamine resin (100-200 ASTM mesh, Bachem) was subjected to solid phase synthesis using the above protocol as in Example 5. Three coupling cycles were performed of one cycle each with Boc-Thr(Bzl) (309 mg, 1.0 mmol), Boc-Gly (175 mg, 1.0 mmol), and Boc-Gly (175 mg, 1.0 mmol). Twenty-eight coupling cycles were performed as in Example 45, except that Boc-m-F-Tyr (Bzl) in the seventh cycle was replaced by Boc-Tyr(2,6-DCB) (440 mg, 1.0 mmol). The peptide-resin (700 mg) was deblocked as in Example 5 to yield 200 mg of crude peptide. Purification by HPLC, as in Example 5, yielded 63.8 mg of a white, amorphous powder. The compound was homogeneous by HPLC and gave a correct amino acid analysis. FAB-MS: MH calc. 3511.0, found 3510.1.

EXAMPLE 49

Ac-[Lys$^{12}$,Nle$^{17}$,Val$^{26}$,Thr$^{28}$,Ala$^{29,30}$,Met$^{31}$]-VIP

A 0.188 g (0.075 mmol) portion of benzhydrylamine resin (100-200 ASTM mesh, Advanced ChemTech) was subjected to solid Phase synthesis as in Example 46, except that Boc-Gly in the second and third cycles were replaced by Boc-Ala (142 mg, 0.75 mmol). The peptide-resin (447 mg) was deblocked as in Example 5 to yield 192 mg of crude peptide. Purification by HPLC, as in Example 5, yielded 10.8 mg of a white, amorphous powder. The compound was homogeneous by HPLC and gave a correct amino acid analysis. FAB-MS: MH calc. 3569.1, found 3568.9.

EXAMPLE 50

Ac-[Lys$^{12}$,Nle$^{17}$,Val$^{26}$,Thr$^{28}$,Ala$^{29-31}$]-VIP

A 0.25 g (0.05 mmol) portion of Boc-Ala-BHA resin from Example 1 was subjected to solid phase synthesis as in Example 5, except that prior to the twenty-seven cycles in Example 5, three cycles were performed of one cycle each with Boc-Ala (95 mg, 0.5 mmol), Boc-Ala (95 mg, 0.5 mmol), and Boc-Thr(Bzl) (155 mg, 0.5 mmol). The peptide-resin (431 mg) was deblocked as in Example 5 to yield 117 mg of crude peptide. Purification by HPLC, as in Example 5, yielded 28.8 mg of a white, amorphous powder. The compound was homogeneous by HPLC and gave a correct amino acid analysis. FAB-MS: MH calc. 3509.0, found 3508.2.

EXAMPLE 51

Ac-[Lys$^{12}$,Nle$^{17}$,Val$^{26}$,Thr$^{28}$Gly$^{29}$,Lys$^{30}$]-VIP

A 0.4 g (0.1 mmol) portion of benzhydrylamine resin (100-200 ASTM mesh, Bachem) was subjected to solid phase synthesis using the above protocol as in Example 5. Two coupling cycles were performed of one cycle each with Boc-Lys(2-Cl-Z) (415 mg, 1.0 mmol), and Boc-Gly (175 mg, 1.0 mmol). Twenty-eight coupling cycles were performed as in Example 45, except that Boc-m-F-Tyr(Bzl) in the seventh cycle was replaced by Boc-Tyr(2,6-DCB) (440 mg, 1.0 mmol). The peptide-resin (873 mg) was deblocked as in Example 5 to yield 272 mg of crude peptide. Purification by HPLC, as in Example 5, yielded 59.0 mg of a white, amorphous powder. The compound was homogeneous by HPLC and gave a correct amino acid analysis. FAB-MS: MH calc. 3481.0, found 3481.3.

EXAMPLE 52

Ac-[Lys$^{12,14}$,Nle$^{17}$,Ala$^{19}$,Val$^{26}$,Thr$^{28}$]-VIP

A 0.4 g (0.1 mmol) portion of benzhydrylamine resin (100-200 ASTM mesh, Bachem) was subjected to solid phase synthesis using the above protocol as in Example 5. Twenty-eight coupling cycles were performed as in Example 45, except that Boc-m-F-Tyr(Bzl) in the seventh cycle was replaced by Boc-Tyr(2,6-DCB) (440 mg, 1.0 mmol), Boc-Val in the tenth cycle was replaced by Boc-Ala (189 mg, 1.0 mmol), and Boc-Arg(Tos) in the fifteenth cycle was replaced by Boc-Lys(2-Cl-Z) (415 mg, 1.0 mmol). The peptide-resin (778 mg) was deblocked as in Example 5 to yield 158 mg of crude peptide. Purification by HPLC, as in Example 5, yielded 31.7 mg of a white, amorphous powder. The compound was homogeneous by HPLC and gave a correct amino acid analysis. FAB-MS: MH calc. 3239.7, found 3239.9.

EXAMPLE 53

Ac-[2-Nal$^{10}$,Lys$^{12}$,Ala$^{17}$,Val$^{26}$,Thr$^{28}$]-VIP

A 0.4 g (0.1 mmol) portion of benzhydrylamine resin (100-200 ASTM mesh, Bachem) was subjected to solid phase synthesis using the above protocol as in Example 5. Twenty-eight coupling cycles were performed as in Example 45, except that Boc-m-F-Tyr(Bzl) in the seventh cycle was replaced by Boc-Tyr(2,6-DCB) (440 mg, 1.0 mmol), Boc-Nle in the twelfth cycle was replaced by Boc-Ala (189 mg, 1.0 mmol), and Boc-Tyr(2,6-DCB) in the nineteenth cycle was replaced by Boc-2-Nal (315 mg, 1.0 mmol). The peptide-resin (600 mg) was deblocked as in Example 5 to yield 210 mg of crude peptide. Purification by HPLC, as in Example 5, yielded 26.5 mg of a white, amorphous powder. The compound was homogeneous by HPLC and gave a correct amino acid analysis. FAB-MS: MH calc. 3287.8, found 3287.5.

EXAMPLE 54

Ac-[Glu$^{8}$,Lys$^{12}$,Nle$^{17}$,Val$^{26}$,Thr$^{28}$, Ala$^{29,30}$,Met$^{31}$]-VIP

A 0.4 g (0.1 mmol) portion of benzhydrylamine resin (100-200 ASTM mesh, Bachem) was subjected to solid phase synthesis using the above protocol as in Example 5. Three coupling cycles were performed of one cycle each with Boc-Met (249 mg, 1.0 mmol), Boc-Gly (175 mg, 1.0 mmol), and Boc-Gly (175 mg, 1.0 mmol). Twenty-eight coupling cycles were performed as in Example 45, except that Boc-m-F-Tyr(Bzl) in the seventh cycle was replaced by Boc-Tyr(2,6-DCB) (440 mg, 1.0 mmol) and Boc-Asp(OcHx) in the twenty-first cycle was replaced by Boc-Glu(Bzl) (337 mg, 1.0 mmol). The peptide-resin (651 mg) was deblocked as in Example 5 to yield 185 mg of crude peptide. Purification by HPLC, as in Example 5, yielded 22 mg of a white, amorphous powder. The compound was homogeneous by HPLC and gave a correct amino acid analysis. FAB-MS: MH calc. 3583.2, found 3582.5.

EXAMPLE 55

Ac-[Glu$^8$,Lys$^{12}$,Nle$^{17}$,Val$^{26}$,Thr$^{28}$,Gly$^{29,30}$,Phe$^{31}$]-VIP

A 0.188 g (0.075 mmol) portion of benzhydrylamine resin (100-200 ASTM mesh, Advanced ChemTech) was subjected to solid phase synthesis as in Example 46, except that Boc-Met in the first cycle was replaced by Boc-Phe (199 mg, 0.75 mmol) and Boc-Asp(OcHx) in the twenty-first cycle was replaced by Boc-Glu(Bzl) (253 mg, 0.75 mmol). The peptide-resin was deblocked as in Example 5 to yield 78 mg of crude peptide. Purification by HPLC, as in Example 5, yielded 8.0 mg of a white, amorphous powder. The compound was homogeneous by HPLC and gave a correct amino acid analysis. FAB-MS: MH calc. 3571.0, found 3569.8.

EXAMPLE 56

Ac-[p-F-Phe$^6$,Glu$^8$,Lys$^{12}$,Nle$^{17}$,Ala$^{19}$,Val$^{26}$,Thr$^{28}$,Gly$^{29,30}$,Cys(Acm)$^{31}$]-VIP

A 0.4 g (0.1 mmol) portion of benzhydrylamine resin (100-200 ASTM mesh, Bachem) was subjected to solid phase synthesis using the above protocol as in Example 5. Three coupling cycles were performed of one cycle each with Boc-Cys(Acm) (292 mg, 1.0 mmol), Boc-Gly (175 mg, 1.0 mmol), and Boc-Gly (175 mg, 1.0 mmol). Twenty-eight coupling cycles were performed as in Example 45, except that Boc-m-F-Tyr(Bzl) in the seventh cycle was replaced by Boc-Tyr(2,6-DCB) (440 mg, 1.0 mmol), Boc-Val in the tenth cycle was replaced by Boc-Ala (189 mg, 1.0 mmol), Boc-Asp(OcHx) in the twenty-first cycle was replaced by Boc-Glu(Bzl) (337 mg, 1.0 mmol), and Boc-Phe in the twenty-third cycle was replaced by Boc-p-F-Phe (142 mg, 0.5 mmol). The peptide-resin (699 mg) was deblocked as in Example 5 to yield 270 mg of crude peptide. Purification by HPLC, as in Example 5, yielded 36.5 mg of a white, amorphous powder. The compound was homogeneous by HPLC and gave a correct amino acid analysis. FAB-MS: MH calc. 3588.1, found 3587.7.

EXAMPLE 57

Ac-[p-F-Phe$^6$,p-NH$_2$-Phe$^{10}$,Lys$^{12}$,Nle$^{17}$,Val$^{26}$,Thr$^{28}$]-VIP

A 0.85 g (0.4 mmol) portion of Boc-Thr(Bzl)-BHA resin from Example 35 was subjected to solid phase synthesis on an Applied Biosystems model 430A peptide synthesizer. Seventeen coupling cycles were performed as in Example 40 to give 2.28 g of Boc-octadecapeptide resin.

A 0.57 g (0.1 mmol) portion of this resin was subjected to solid phase synthesis as in Example 15 and carried through ten cycles of one cycle each with Boc-p-NH(Z)-Phe (166 mg, 0.4 mmol), Boc-Asn (102 mg, 0.44 mmol), Boc-Asp(OcHx) (126 mg, 0.4 mmol), Boc-Thr(Bzl) (124 mg, 0.4 mmol), Boc-p-F-Phe (113 mg, 0.4 mmol), Boc-Val (87 mg, 0.4 mmol), Boc-Ala (76 mg, 0.4 mmol), Boc-Asp(OcHx) (126 mg, 0.4 mmol), Boc-Ser(Bzl) (118 mg, 0.4 mmol), and Boc-His(Tos) (164 mg, 0.4 mmol). The peptide resin was carried through protocol steps 1-8 and treated with 0.5 mL acetic anhydride in 20 mL 6% DIPEA/methylene chloride for 30 minutes. The resin was washed using steps 10-14 and dried under vacuum to yield 603 mg. The peptide-resin was deblocked as in Example 5 to yield 252 mg of crude peptide. The peptide was purified as in Example 5 to yield 40.4 mg of a white, amorphous powder. The compound was homogeneous by HPLC and gave a correct amino acid analysis. FAB-MS: MH calc. 3312.8, found 3312.6.

EXAMPLE 58

Ac-[Lys$^{12}$,Ala$^{17}$,Val$^{26}$,Gly$^{29,30}$,Cys(Acm)$^{31}$]-VIP

A 1.0 g (0.44 mmol) portion of the Boc-Cys(Acm)-BHA resin from Example 47 was subjected to solid phase synthesis on a Biosearch model 9500 peptide synthesizer. Thirty coupling cycles were Performed as in Example 47 except that Boc-Nle in cycle fourteen was replaced by Boc-Ala (500 mg, 2.6 mmol). The peptide resin was deprotected and treated with acetic anhydride 30 minutes. The resin was dried under vacuum to yield 2.4 g of peptide resin.

A 1.2 g portion of this peptide resin was deblocked as in Example 11 to yield 370 mg of crude peptide. Purification by HPLC, as in Example 5, yielded 70 mg of a white, amorphous powder. The compound was homogeneous by HPLC and gave a correct amino acid analysis. FAB-MS: MH calc. 3542.0, found 3541.7.

EXAMPLE 59

Ac-[Glu$^8$,Lys$^{12,14}$,Nle$^{17}$,Val$^{26}$,Thr$^{28}$,Gly$^{29,30}$,Met$^{31}$]-VIP

A 0.4 g (0.1 mmol) portion of benzhydrylamine resin (100-200 ASTM mesh, Bachem) was subjected to solid phase synthesis using the above protocol as in Example 5. Three coupling cycles were performed of one cycle each with Boc-Met (249 mg, 1.0 mmol), Boc-Gly (175 mg, 1.0 mmol), and Boc-Gly (175 mg, 1.0 mmol). Twenty-eight coupling cycles were performed as in Example 45, except that Boc-m-F-Tyr(Bzl) in the seventh cycle was replaced by Boc-Tyr(2,6-DCB) (440 mg, 1.0 mmol), Boc-Arg(Tos) in the fifteenth cycle was replaced by Boc-Lys(2-Cl-Z) (415 mg, 1.0 mmol), and Boc-Asp(OcHx) in the twenty-first cycle was replaced by Boc-Glu(Bzl) (337 mg, 1.0 mmol). The peptide-resin (814 mg) was deblocked as in Example 5 to yield 200 mg of crude peptide. Purification by HPLC, as in Example 5, yielded 20.6 mg of a white, amorphous powder. The compound was homogeneous by HPLC and gave a correct amino acid analysis. FAB-MS: MH calc. 3527.1, found 3526.7.

EXAMPLE 60

Ac-[p-NH$_2$-Phe$^{10}$,Lys$^{12}$,Nle$^{17}$,Ala$^{19}$,Val$^{26}$,Thr$^{28}$]-VIP

A 0.4 g (0.1 mmol) portion of benzhydrylamine resin (100-200 ASTM mesh, Bachem) was subjected to solid phase synthesis using the above protocol as in Example 5. Twenty-eight coupling cycles were performed as in Example 45, except that Boc-m-F-Tyr(Bzl) in the seventh cycle was replaced by Boc-Tyr(2,6-DCB) (440 mg, 1.0 mmol), Boc-Val in the tenth cycle was replaced by Boc-Ala (189 mg, 1.0 mmol), and Boc-Tyr(2,6-DCB) in the ninteenth cycle was replaced by Boc-p-NH(Z)-Phe (208 mg, 0.5 mmol). The peptide-resin was deblocked as in Example 5 to yield 138 mg of crude peptide. Purification by HPLC, as in Example 5, yielded 23.1 mg of a white, amorphous powder. The compound was homogeneous by HPLC and gave a correct amino acid analysis. FAB-MS: MH calc. 3266.7, found 3266.6.

EXAMPLE 61

Ac-[p-F-Phe$^6$,Glu$^8$,Lys$^{12}$,Nle$^{17}$,Val$^{26}$,Thr$^{28}$,Gly$^{29,30}$,Cys(Acm)$^{31}$]-VIP

A 0.4 g (0.1 mmol) portion of benzhydrylamine resin (100–200 ASTM mesh, Bachem) was subjected to solid phase synthesis using the above protocol as in Example 5. Three coupling cycles were performed of one cycle each with Boc-Cys(Acm) (292 mg, 1.0 mmol), Boc-Gly (175 mg, 1.0 mmol), and Boc-Gly (175 mg, 1.0 mmol). Twenty-eight coupling cycles were performed as in Example 45, except that Boc-m-F-Tyr(Bzl) in the seventh cycle was replaced by Boc-Tyr(2,6-DCB) (440 mg, 1.0 mmol), Boc-Asp(OcHx) in the twenty-first cycle was replaced by Boc-Glu(Bzl) (337 mg, 1.0 mmol), Boc-Phe in the twenty-third cycle was replaced by Boc-p-F-Phe (142 mg, 0.5 mmol). The peptide-resin (900 mg) was deblocked as in Example 5 to yield 255 mg of crude peptide. Purification by HPLC, as in Example 5, yielded 20.5 mg of a white, amorphous powder. The compound was homogeneous by HPLC and gave a correct amino acid analysis. FAB-MS MH calc. 3616.1, found 3615.6.

EXAMPLE 62

Ac-[Glu$^8$,Lys$^{12}$,Ala$^{17,19}$,Val$^{26}$,Thr$^{28}$,Gly$^{29,30}$,Met$^{31}$]-VIP

A 0.4 g (0.1 mmol) portion of benzhydrylamine resin (100–200 ASTM mesh, Bachem) was subjected to solid phase synthesis using the above protocol as in Example 5. Three coupling cycles were performed of one cycle each with Boc-Met (249 mg, 1.0 mmol), Boc-Gly (175 mg, 1.0 mmol), and Boc-Gly (175 mg, 1.0 mmol). Twenty-eight coupling cycles were performed as in Example 45, except that Boc-m-F-Tyr(Bzl) in the seventh cycle was replaced by Boc-Tyr(2,6-DCB) (440 mg, 1.0 mmol), Boc-Val in the tenth cycle was replaced by Boc-Ala (189 mg, 1.0 mmol), Boc-Nle in the twelfth cycle was replaced by Boc-Ala (189 mg, 1.0 mmol), and Boc-Asp(OcHx) in the twenty-first cycle was replaced by Boc-Glu(Bzl) (337 mg, 1.0 mmol). The peptide-resin (736 mg) was deblocked as in Example 5 to yield 240 mg of crude peptide. Purification by HPLC, as in Example 5, yielded 38.8 mg of a white, amorphous powder. The compound was homogeneous by HPLC and gave a correct amino acid analysis. FAB-MS: MH calc. 3485.0, found 3484.6.

EXAMPLE 63

Ac-[Glu$^8$,Lys$^{12}$,Nle$^{17}$,Val$^{26}$,Thr$^{28}$,Gly$^{29,30}$,Ala$^{31}$]-VIP

A 0.25 g (0.05 mmol) portion of Boc-Ala resin from Example 1 was subjected to solid phase synthesis using the above protocol as in Example 5. Three coupling cycles were performed of one cycle each with Boc-Gly (87 mg, 0.5 mmol), Boc-Gly (87 mg, 0.5 mmol), and Boc-Thr(Bzl) (155 mg, 0.5 mmol). Twenty-seven coupling cycles were performed as in Example 5, except that Boc-Asp(OcHx) in the twentieth cycle was replaced by Boc-Glu(Bzl) (167 mg, 0.5 mmol). The peptide-resin (380 mg) was deblocked as in Example 5 to yield 115 mg of crude peptide. Purification by HPLC yielded 31.6 mg of a white, amorphous powder. The compound was homogeneous by HPLC and gave a correct amino acid analysis. FAB-MS MH calc. 3495.0, found 3495.1.

EXAMPLE 64

Ac-[Glu$^8$,Lys$^{12}$,Nle$^{17}$,Ala$^{19}$,Val$^{26}$,Thr$^{28}$,Gly$^{29,30}$,Met$^{31}$]-VIP

A 0.4 g (0.1 mmol) portion of benzhydrylamine resin (100–200 ASTM mesh, Bachem) was subjected to solid phase synthesis using the above protocol as in Example 5. Three coupling cycles were performed of one cycle each with Boc-Met (249 mg, 1.0 mmol), Boc-Gly (175 mg, 1.0 mmol), and Boc-Gly (175 mg, 1.0 mmol). Twenty-eight coupling cycles were performed as in Example 45, except that Boc-m-F-Tyr(Bzl) in the seventh cycle was replaced by Boc-Tyr(2,6-DCB) (440 mg, 1.0 mmol), Boc-Val in the tenth cycle was replaced by Boc-Ala (189 mg, 1.0 mmol), and Boc-Asp(OcHx) in the twenty-first cycle was replaced by Boc-Glu(Bzl) (337 mg, 1.0 mmol). The peptide-resin (800 mg) was deblocked as in Example 5 to yield 200 mg of crude peptide. Purification by HPLC, as in Example 5, yielded 20.8 mg of a white, amorphous powder. The compound was homogeneous by HPLC and gave a correct amino acid analysis. FAB-MS: MH calc. 3527.1, found 3527.1.

EXAMPLE 65

Ac-[p-F-Phe$^6$,Lys$^{12}$,Nle$^{17}$,Ala$^{19}$,Val$^{26}$,Thr$^{28}$,Gly$^{29,30}$,Cys(Acm)$^{31}$]-VIP

A 0.4 g (0.1 mmol) portion of benzhydrylamine resin (100–200 ASTM mesh, Bachem) was subjected to solid phase synthesis using the above protocol as in Example 5. Three coupling cycles were performed of one cycle each with Boc-Cys(Acm) (292 mg, 1.0 mmol), Boc-Gly (175 mg, 1.0 mmol), and Boc-Gly (175 mg, 1.0 mmol). Twenty-eight coupling cycles were performed as in Example 45, except that Boc-m-F-Tyr(Bzl) in the seventh cycle was replaced by Boc-Tyr(2,6-DCB) (440 mg, 1.0 mmol), Boc-Val in the tenth cycle was replaced by Boc-Ala (189 mg, 1.0 mmol), and Boc-Phe in the twenty-third cycle was replaced by Boc-p-F-Phe (142 mg, 0.5 mmol). The peptide-resin (708 mg) was deblocked as in Example 5 to yield 263 mg of crude peptide. Purification by HPLC, as in Example 5, yielded 48.8 mg of a white, amorphous powder. The compound was homogeneous by HPLC and gave a correct amino acid analysis. FAB-MS: MH calc. 3574.1, found 3573.9.

EXAMPLE 66

Ac-[Glu$^8$,Lys$^{12}$,Nle$^{17}$,Val$^{26}$,Thr$^{28}$,Gly$^{29,30}$,Ser$^{31}$]-VIP

A 0.313 g (0.05 mmol) portion of Boc-Ser(Bzl) resin from Example 3 was subjected to solid phase synthesis using the above protocol as in Example 5. Three coupling cycles were performed of one cycle each with Boc-Gly (87 mg, 0.5 mmol), Boc-Gly (87 mg, 0.5 mmol), and Boc-Thr(Bzl) (155 mg, 0.5 mmol). Twenty-seven coupling cycles were performed as in Example 5, except that Boc-Asp(OcHx) in the twentieth cycle was replaced by Boc-Glu(Bzl) (167 mg, 0.5 mmol) The peptide-resin (511 mg) was deblocked as in Example 5 to yield 148 mg of crude peptide. Purification by HPLC yielded 56.7 mg of a white, amorphous powder. The compound was homogeneous by HPLC and gave a correct amino acid analysis. FAB-MS: MH calc. 3511.0, found 3510.3.

EXAMPLE 67

Ac-[p-F-Phe$^6$,Glu$^8$,Lys$^{12}$,Nle$^{17}$,Ala$^{19}$,Val$^{26}$,Thr$^{28}$]-VIP

A 0.4 g (0.1 mmol) portion of benzhydrylamine resin (100–200 ASTM mesh, Bachem) was subjected to solid phase synthesis using the above protocol as in Example 5. Twenty-eight coupling cycles were performed as in Example 45, except that Boc-m-F-Tyr(Bzl) in the seventh cycle was replaced by Boc-Tyr(2,6-DCB) (440 mg, 1.0 mmol), Boc-Val in the tenth cycle was replaced by Boc-Ala (189 mg, 1.0 mmol), Boc-Asp(OcHx) in the twenty-first cycle was replaced by Boc-Glu(Bzl) (337 mg, 1.0 mmol), and Boc-Phe in the twenty-third cycle was replaced by Boc-p-F-Phe (142 mg, 0.5 mmol). The peptide-resin (700 mg) was deblocked as in Example 5 to yield 230 mg of crude peptide. Purification by HPLC, as in Example 5, yielded 52.5 mg of a white, amorphous powder. The compound was homogeneous by HPLC and gave a correct amino acid analysis. FAB-MS: MH calc. 3299.8, found 3299.6.

EXAMPLE 68

Ac-[Glu$^8$,Orn$^{12}$,Nle$^{17}$,Val$^{26}$,Thr$^{28}$]-VIP

A 5.5 g (0.6 mmol) portion of the Boc-dodecapeptide resin from Example 22 was carried through four coupling cycles of one cycle each with Boc-Gln (655 mg, 2.66 mmol), Boc-Lys(2-Cl-Z) (2.01 g, 4.84 mmol), Boc-Arg(Tos) (2.07 g, 4.84 mmol), and Boc-Leu (1.21 g, 4.84 mmol). The resin was dried under vacuum to give 6.12 g of Boc-hexadecapeptide resin.

A 2.0 g (0.2 mmol) portion of this resin was carried through twelve coupling cycles of one cycle each with Boc-Orn(Fmoc) (182 mg, 0.4 mmol), Boc-Thr(Bzl) (250 mg, 0.8 mmol), Boc-Tyr(2,6-DCB) (352 mg, 0.8 mmol), Boc-Asn (102 mg, 0.44 mmol), Boc-Glu(OFm) (340 mg, 0.8 mmol), Boc-Thr(Bzl) (248 mg, 0.8 mmol), Boc-Phe (212 mg, 0.8 mmol), Boc-Val (174 mg, 0.8 mmol), Boc-Ala (152 mg, 0.8 mmol), Boc-Asp(OcHx) (252 mg, 0.8 mmol), Boc-Ser(Bzl) (236 mg, 0.8 mmol), and Boc-His(-Bom) (150 mg, 0.4 mmol). The peptide resin was carried through protocol steps 1–8 and treated with 0.5 mL acetic anhydride and 38.4 mL DIPEA in 30 mL methylene chloride for 90 minutes. The resin was washed using steps 10–14 and dried under vacuum to yield 2.4 g.

A 1.2 g (0.1 mmol) portion of this resin was treated twice with 20% piperidine/DMF for 1 minute and 20 minutes, respectively, and washed using steps 10–14. The peptide-resin was deblocked as in Example 5 to yield 420 mg of crude peptide. Purification by HPLC, as in Example 5, yielded 63.1 mg of a white, amorphous powder. The compound was homogeneous by HPLC and gave a correct amino acid analysis. FAB-MS: MH calc. 3295.8, found 3295.6.

EXAMPLE 69

Ac-[Lys$^{12}$,Nle$^{17}$,Ala$^{25}$,Leu$^{26}$,Lys$^{27,28}$,Gly$^{29,30}$,Thr$^{31}$]-VIP

A 0.4 g (0.1 mmol) portion of benzhydrylamine resin (100–200 ASTM mesh, Bachem) was subjected to solid phase synthesis using the above protocol as in Example 5. Three coupling cycles were performed of one cycle each with Boc-Thr(Bzl) (309 mg, 1.0 mmol), Boc-Gly (175 mg, 1.0 mmol), and Boc-Gly (175 mg, 1.0 mmol). Twenty-eight coupling cycles were performed as in Example 45, except that Boc-Thr(Bzl) and Boc-Leu in the first and second cycles were each replaced with Boc-Lys(2-Cl-Z) (415 mg, 1.0 mmol), Boc-Val in the third cycles was replaced by Boc-Leu (249 mg, 1.0 mmol), Boc-Ser(Bzl) in the fourth cycle was replaced by Boc-Ala (189 mg, 1.0 mmol), and Boc-m-F-Tyr(Bzl) in the seventh cycle was replaced by Boc-Tyr(2,6-DCB) (440 mg, 1.0 mmol). The peptide-resin (700 mg) was deblocked as in Example 5 to yield 140 mg of crude peptide. Purification by HPLC, as in Example 5, yielded 31.0 mg of a white, amorphous powder. The compound was homogeneous by HPLC and gave a correct amino acid analysis. FAB-MS: MH calc. 3551.1, found 3550.8.

EXAMPLE 70

Ac-[Glu$^8$,Lys$^{12}$,Nle$^{17}$,Val$^{26}$,Thr$^{28}$,Ala$^{29\text{-}31}$]-VIP A 0.251 g (0.05 mmol) portion of Boc-Ala resin from Example 1 was subjected to solid phase synthesis using the above protocol as in Example 5. Three coupling cycles were performed of one cycle each with Boc-Ala (95 mg, 0.5 mmol), Boc-Ala (95 mg, 0.5 mmol), and Boc-Thr(Bzl) (155 mg, 0.5 mmol). Twenty-seven coupling cycles were performed as in Example 5, except that Boc-Asp(OcHx) in the twentieth cycle was replaced by Boc-Glu(Bzl) (167 mg, 0.5 mmol) The peptide-resin (399 mg) was deblocked as in Example 5 to yield 63.1 mg of crude peptide. Purification by HPLC yielded 19.0 mg of a white, amorphous powder. The compound was homogeneous by HPLC and gave a correct amino acid analysis. FAB-MS: MH calc. 3523.0, found 3522.5.

EXAMPLE 71

Ac-[Lys$^{12}$,Ala$^{17,19}$,Val$^{26}$,Thr$^{28}$]-VIP

A 0.4 g (0.1 mmol) portion of benzhydrylamine resin (100–200 ASTM mesh, Bachem) was subjected to solid phase synthesis using the above protocol as in Example 5. Twenty-eight coupling cycles were performed as in Example 45, except that Boc-m-F-Tyr(Bzl) in the seventh cycle was replaced by Boc-Tyr(2,6-DCB) (440 mg, 1.0 mmol), and Boc-Val in the tenth cycle and Boc-Nle in the twelfth cycle were each replaced by Boc-Ala (189 mg, 1.0 mmol). The peptide-resin was deblocked as in Example 5 to yield 200 mg of crude peptide. Purification by HPLC, as in Example 5, yielded 52.4 mg of a white, amorphous powder. The compound was homogeneous by HPLC and gave a correct amino acid analysis. FAB-MS: MH calc. 3225.7, found 3226.0.

EXAMPLE 72

Ac-[Glu$^8$,Lys$^{12}$,Nle$^{17}$,Val$^{26}$,Thr$^{28}$,Gly$^{29}$,Lys$^{30}$]-VIP

A 0.4 g (0.1 mmol) portion of benzhydrylamine resin 100–200 ASTM mesh, Bachem) was subjected to solid phase synthesis using the above protocol as in Example 5. Two coupling cycles were performed of one cycle each with Boc-Lys(2-Cl-Z) (415 mg, 1.0 mmol), and Boc-Gly (175 mg, 1.0 mmol). Twenty-eight coupling cycles were performed as in Example 45, except that Boc-m-F-Tyr(Bzl) in the seventh cycle was replaced by Boc-Tyr(2,6-DCB) (440 mg, 1.0 mmol), and Boc-Asp(OcHx) in the twenty-first cycle was replaced by Boc-Glu(Bzl) (337 mg, 1.0 mmol). The peptide-resin (870 mg) was deblocked as in Example 5 to yield 206 mg of crude peptide. Purification by HPLC, as in Example 5, yielded 65.7 mg of a white, amorphous powder. The compound was homogeneous by HPLC and gave a correct amino acid analysis. FAB-MS: MH calc. 3495.0, found 3494.6.

EXAMPLE 73

Ac-[p-NH$_2$-Phe$^{10}$,Lys$^{12}$,Nle$^{17}$,Val$^{26}$,Thr$^{28}$,Gly$^{29,30}$,Cys(Acm)$^{31}$]-VIP

A 0.25 g (0.05 mmol) portion of benzhydrylamine resin 100–200 ASTM mesh, Advanced ChemTech) was subjected to solid phase synthesis using the above protocol as in Example 5. Four coupling cycles were performed of one cycle each with Boc-Cys(Acm) (146 mg, 0.5 mmol), Boc-Gly (87 mg, 0.5 mmol), Boc-Gly (87 mg, 0.5 mmol) and Boc-Thr(Bzl) (155 mg, 0.5 mmol). Twenty-seven coupling cycles were performed as in Example 5, except that Boc-Tyr(2,6-DCB) in the eighteenth cycle was replaced by Boc-p-NH(Z)-Phe (207 mg, 0.5 mmol). The peptide-resin was deblocked as in Example 5 to yield 294 mg of crude Peptide. Purification by HPLC, as in Example 5, yielded 20.1 mg of a white, amorphous powder. The compound was homogeneous by HPLC and gave a correct amino acid analysis. FAB-MS: MH calc. 3583.1, found 3582.8.

EXAMPLE 74

Ac-[Glu$^8$,Lys$^{12}$,Nle$^{17}$,Val$^{26}$,Thr$^{28}$,Gly$^{29,30}$,Cys(Acm)$^{31}$]-VIP

A 0.4 g (0.1 mmol) portion of benzhydrylamine resin (100–200 ASTM mesh, Bachem) was subjected to solid phase synthesis using the above protocol as in Example 5. Three coupling cycles were performed of one cycle each with Boc-Cys(Acm) (292 mg, 1.0 mmol), Boc-Gly (175 mg, 1.0 mmol), and Boc-Gly (175 mg, 1.0 mmol). Twenty-eight coupling cycles were performed as in Example 45, except that Boc-m-F-Tyr(Bzl) in the seventh cycle was replaced by Boc-Tyr(2,6-DCB) (440 mg, 1.0 mmol), and Boc-Asp(OcHx) in the twenty-first cycle was replaced by Boc-Glu(Bzl) (337 mg, 1.0 mmol). The peptide-resin was deblocked as in Example 5 to yield 450 mg of crude peptide. Purification by HPLC. as in Example 5, yielded 108 mg of a white, amorphous powder. The compound was homogeneous by HPLC and gave a correct amino acid analysis. FAB-MS: MH calc. 3598.2, found 3598.0.

EXAMPLE 75

Ac-[Glu$^8$,Lys$^{12}$,Nle$^{17}$,Val$^{26}$,Thr$^{28}$,Gly$^{29,30}$,Met$^{31}$]-VIP

A 0.269 g (0.05 mmol) portion of Boc-Met resin from Example 4 was subjected to solid phase synthesis using the above protocol as in Example 5. Three coupling cycles were performed of one cycle each with Boc-Gly (87 mg, 0.5 mmol), Boc-Gly (87 mg, 0.5 mmol), and Boc-Thr(Bzl) (155 mg, 0.5 mmol). Twenty-seven coupling cycles were performed as in Example 5, except that Boc-Asp(OcHx) in the twentieth cycle was replaced by Boc-Glu(Bzl) (167 mg, 0.5 mmol) The peptide-resin (906 mg) was deblocked as in Example 5 to yield 128 mg of crude peptide. Purification by HPLC yielded 24.2 mg of a white, amorphous powder. A 21.2 mg portion of this material was treated with 0.9 mL B-mercaptoethanol in 2.1 mL H$_2$O at 37° C for 48 hours. repurified by HPLC as in Example 5 to yield 13.1 mg of a white, amorphous powder. The compound was homogeneous by HPLC and gave a correct amino acid analysis. FAB-MS: MH calc. 3550.1, found 3550.0.

EXAMPLE 76

CH$_3$S(CH$_2$)$_2$CO-[Lys$^{12}$,Nle$^{17}$,Val$^{26}$,Thr$^{28}$]-VIP(2-28)

A 0.85 g (0.4 mmol) portion of the Boc-Thr(Bzl)-BHA resin from Example 35 was subjected to solid phase synthesis on an Applied Biosystems model 430A peptide synthesizer as in Example 11. Twenty-six coupling cycles were performed of one cycle each with Boc-Leu (499 mg, 2.0 mmol), Boc-Val (435 mg, 2.0 mmol), Boc-Ser(Bzl) (590 mg, 2.0 mmol), Boc-Asn (464 mg, 2.0 mmol), Boc-Leu (499 mg, 2.0 mmol), Boc-Tyr(2,6-DCB) (880 mg, 2.0 mmol), Boc-Lys(2-Cl-Z) (830 mg, 2.0 mmol), Boc-Lys(2-Cl-Z) (830 mg, 2.0 mmol), Boc-Val (435 mg, 2.0 mmol), Boc-Ala (378 mg, 2.0 mmol), Boc-Nle (462 mg, 2.0 mmol), Boc-Gln (492 mg, 2.0 mmol), Boc-Lys(2-Cl-Z) (830 mg, 2.0 mmol), Boc-Arg(Tos) (856 mg, 2.0 mmol), Boc-Leu (499 mg, 2.0 mmol), Boc-Lys(2-Cl-Z) (830 mg, 2.0 mmol), Boc-Thr(Bzl) (618 mg, 2.0 mmol), Boc-Tyr(2,6-DCB) (880 mg, 2.0 mmol), Boc-Asn (232 mg, 2.0 mmol), Boc-Asp(OcHx) (631 mg, 2.0 mmol), Boc-Thr(Bzl) (618 mg, 2.0 mmol), Boc-Phe (531 mg, 2.0 mmol), Boc-Val (435 mg, 2.0 mmol), Boc-Ala (378 mg, 2.0 mmol), Boc-Asp(OcHx) (631 mg, 2.0 mmol), and Boc-Ser(Bzl) (591 mg, 2.0 mmol) to give 2.8 g of Boc-heptacosapeptide resin.

A 0.7 g (0.1 mmol) portion of this resin was carried through protocol steps 1–8 and treated with 128 mg (1.06 mmol) of 3-(methylthio)propionic acid and 110 mg (0.53 mmol) of dicyclohexylcarbodiimide in 20 mL methylene chloride for hours. The resin was washed using steps 10–14 and dried under vacuum. The peptide-resin (588 mg) was deblocked as in Example 5 to yield 245 mg of crude peptide. The peptide was purified by HPLC as in Example 5 to yield 28.8 mg of a white, amorphous powder. The compound was homogeneous by HPLC and gave a correct amino acid analysis. FAB-MS: MH calc. 3218.8, found 3218.5.

EXAMPLE 77

CH$_3$SO(CH$_2$)$_2$CO-[Lys$^{12}$,Nle$^{17}$,Val$^{26}$,Thr$^{28}$]-VIP(2-28)

20.0 mg (6.2 mmol) of CH$_3$S(CH$_2$)$_2$CO-[Lys$^{12}$Nle$^{17}$,Val$^{26}$,Thr$^{28}$]-VIP(2-28) from Example 76 was dissolved in 2.0 mL 1% AcOH. TO this was added 764 mL of a 1:100 diluted (H$_2$O) solution of 30% H$_2$O$_2$. This solution was stirred at room temperature for 5 hours and then lyophilized. The peptide was purified by HPLC as in Example 5 to yield 14.6 mg of a white, amorphous powder. The compound was homogeneous by HPLC and gave a correct amino acid analysis. FAB-MS: MH calc. 3234.8, found 3234.6.

EXAMPLE 78

Ac-[N-CH$_3$-Ala$^1$,Lys$^{12}$,Nle$^{17}$,Val$^{26}$,Thr$^{28}$]-VIP

A 2.0 g (0.16 mmol) portion of the Boc-hexacosapeptide resin from Example 32 was carried through two coupling cycles of one cycle each with Boc-Ser(Bzl) (378 mg, 1.28mmol), and Boc-N-CH$_3$-Ala (260 mg, 1.28 mmol). One half of this peptide resin (0.08 mmol) was carried through protocol steps 1–8 and treated with 0.5 mL acetic anhydride in 15 mL 6% DIPEA/methylene chloride for 3.5 hours. The resin was washed using steps 10–14 and dried under vacuum to yield 0.8 g.

The peptide resin was treated with HF as in Example 11 to yield, after lyophilization, 484 mg of a white solid. This crude peptide was purified by preparative HPLC as in Example 5. The main peak was cut by analytical HPLC analysis of collected fractions, pooled and lyophilized to yield 22.5 mg of a white, amorphous powder. This compound was homogeneous by HPLC and gave a correct amino acid analysis. FAB-MS: calc. 3243.8, found 3243.1.

EXAMPLE 79

Boc-Cys(Acm)-BHA Resin 5.0 g (3.5 mequiv) of benzhydrylamine resin (100–200 ASTM mesh, Omni) was treated as in Example 1 except that the resin was coupled with Boc-Cys(Acm) (1.46 g, 5.0 mmole) and dicyclohexylcarbodiimide (516 mg, 2.5 mmole). The resin was dried under vacuum to yield 5.8 g of Boc-Cys(Acm)-BHA resin. Amino acid analysis indicated a loading of 0.19 mmol Cys/g.

EXAMPLE 80

Ac-[Leu$^5$,Orn$^{12}$,Ala$^{17,19}$,Thr$^{25}$,Val$^{26}$,Thr$^{28}$,Gly$^{29,30}$,Cys(Acm)$^{31}$]-VIP

A 0.263 g (0.05 mmol) portion of Boc-Cys(Acm)-BHA resin from Example 79 was subjected to solid phase synthesis using the above protocol as in Example 5. Three coupling cycles were performed of one cycle each with Boc-Gly (87 mg, 0.5 mmol), Boc-Gly (87 mg, 0.5 mmol), and Boc-Thr(Bzl) (155 mg, 0.5 mmol). Twenty-seven coupling cycles were performed as in Example 5, except that Boc-Ser(Bzl) in the third cycle was replaced by Boc-Thr(Bzl) (154 mg, 0.5 mmol), Boc-Val in the nineth cycle and Boc-Nle in the eleventh cycle were each replaced by Boc-Ala (95 mg, 0.5 mmol), Boc-Lys(2-Cl-Z) in the sixteenth cycle was replaced by Boc-Orn(Z) (183 mg, 0.5 mmol), and Boc-Val in the twenty-third cycle was replaced by Boc-Leu (124 mg, 0.5 mmol). The peptide-resin (489 mg) was deblocked as in Example 5 to yield 126 mg of crude peptide. The peptide was purified by HPLC as in Example 5 to yield 6.7 mg of a white, amorphous powder. The compound was homogeneous by HPLC and gave a correct amino acid analysis. FAB-MS: MH calc. 3528.0, found 527.4.

EXAMPLE 81

Ac-[p-F-Phe$^6$,2-Nal$^{10}$,Lys$^{12}$,Nle$^{17}$,Val$^{26}$,Thr$^{28}$,Gly$^{29,30}$,Met$^{31}$]-VIP

A 0.4 g (0.1 mmol) portion of benzhydrylamine resin (100–200 ASTM mesh, Bachem) was subjected to solid phase synthesis using the above protocol as in Example 5. Three coupling cycles were performed of one cycle each with Boc-Met (249 mg, 1.0 mmol), Boc-Gly (175 mg, 1.0 mmol), and Boc-Gly (175 mg, 1.0 mmol). Twenty-eight coupling cycles were performed as in Example 45, except that Boc-m-F-Tyr(Bzl) in the seventh cycle was replaced by Boc-Tyr(2,6-DCB) (440 mg, 1.0 mmol), Boc-Tyr(2,6-DCB) in the nineteenth cycle was replaced by Boc-2-Nal (157 mg, 0.5 mmol), and Boc-Phe in the twenty-third cycle was replaced by Boc-p-F-Phe (283 mg, 1.0 mmol). The peptide-resin (756 mg) was deblocked as in Example 5 to yield 280 mg of crude peptide. Purification by HPLC, as in Example 5, yielded 32.2 mg of a white, amorphous powder. The compound was homogeneous by HPLC and gave a correct amino acid analysis. FAB-MS: MH calc. 3593.1, found 3593.1.

EXAMPLE 82

Ac-[p-F-Phe$^6$,Glu$^8$,Lys$^{12,14}$,Nle$^{17}$,Ala$^{19}$,Val$^{26}$,Thr$^{28}$,Gly$^{29,30}$,Cys(Acm)$^{31}$]-VIP

A 0.4 g (0.1 mmol) portion of benzhydrylamine resin (100–200 ASTM mesh, Bachem) was subjected to solid phase synthesis using the above protocol as in Example 5. Three coupling cycles were performed of one cycle each with Boc-Cys(Acm) (292 mg, 1.0 mmol), Boc-Gly (175 mg, 1.0 mmol), and Boc-Gly (175 mg, 1.0 mmol). Twenty-eight coupling cycles were performed as in Example 45, except that Boc-m-F-Tyr(Bzl) in the seventh cycle was replaced by Boc-Tyr(2,6-DCB) (440 mg, 1.0 mmol), Boc-Val in the tenth cycle was replaced by Boc-Ala (189 mg, 1.0 mmol), Boc-Arg(Tos) in the fifteenth cycle was replaced by Boc-Lys(2-Cl-Z) (415 mg, 1.0 mmol), Boc-Asp(OcHx) in the twenty-first cycle was replaced by Boc-Glu(Bzl) (337 mg, 1.0 mmol), and Boc-Phe in the twenty-third cycle was replaced by Boc-p-F-Phe (142 mg, 0.5 mmol). The peptide-resin (800 mg) was deblocked as in Example 5 to yield 100 mg of crude peptide. Purification by HPLC, as in Example 5, yielded 33.1 mg of a white, amorphous powder. The compound was homogeneous by HPLC and gave a correct amino acid analysis. FAB-MS: MH calc. 3560.1, found 3559.8.

EXAMPLE 83

Tracheal Relaxant Activity of VIP Analogs

The relaxant activity of the VIP analogs was studied in a model utilizing guinea pig trachea. [Wasserman, M. A. et al., in Vasoactive Intestinal Peptide, S. I. Said, ed., Raven Press, N.Y. 1982, pp 177–184]; All tissues were taken from male albino guinea pig weighing 400–600 g, anesthesized with urethane (2 g/kg, i.p.). After exanguination, the trachea were removed and divided into four ring segments (3 mm length). Each ring was suspended by 30 gauge stainless steel wires in a 10 mL jacketed tissue bath and attached via 4-0 silk thread to a Grass force displacement transducer (model FT03C, Grass Instruments Co., Quincy, Ma), for isometric recording of tension. The smooth muscle was bathed in modified Krebs solution of the following composition: NaCl, 120 mM; KCl, 4.7 mM; CaCl$_2$, 2.5 mM; MgSO$_4$.7H$_2$O, 1.2 mM; NaHCO$_3$, 25 mM; K$_2$HPO$_4$ monobasic, 1.2 mM; and dextrose, 10 mM. Tissue baths were maintained at 37° C. and constantly bubbled with 95% O$_2$ and 5% CO$_2$. Responses were recorded on an 8 channel and a 4 channel Hewlett-Packard (model 7702B and 7754A, respectively) recorder (Hewlett-Packard, Paramus, N.J.). Tracheal rings were placed under a resting tension of 1.5 g which was determined to be at or near optimal in preliminary experiments. Frequent readjustments of tension were required during the 60 minute stabilization period which followed. Tissues were rinsed at 15 minute intervals.

Cumulative concentration response curves were obtained for each tissue by successive $\mu\mu L$ increases in the bath concentration of VIP or VIP analogs according to the method of VanRossum [Arch. Int. Pharmacodyn., 143, 299–330 (1963)]. Only one cummulative dose response curve was obtained on a single tissue. To minimize variability between tissues, relaxant responses were expressed as a percentage of the maximum response obtained to VIP ($10^{-6}$M=100%) added at the end of each concentration response experiment. Responses obtained from at least three tissues were pooled and EC$_{50}$ values were determined by linear regression.

The results summarized in Table I show the tracheal relaxant activity of the VIP analogs in comparison to native VIP. The results summarized in Table I show that the VIP analogs have potentials equal to or greater than VIP.

TABLE I

Relaxant Activity of VIP analogs on guinea pig tracheal smooth muscle

| Compound | EC$_{50}$ (nM) |
|---|---|
| VIP | 10.0 |
| Ac-[N-Me-Ala$^1$,Lys$^{12}$,Nle$^{17}$,Val$^{26}$,Thr$^{28}$]-VIP | 7.2 |
| Ac-[Leu$^5$,Orn$^{12}$,Ala$^{17,19}$,Thr$^{25}$,Val$^{26}$,Thr$^{28}$,Gly$^{29,30}$,Cys(Acm)$^{31}$]-VIP | 2.2 |
| Ac-[p-F-Phe$^6$,Glu$^8$,Lys$^{12}$,Nle$^{17}$,Ala$^{19}$,Val$^{26}$,Thr$^{28}$,Gly$^{29,30}$,Cys(Acm)$^{31}$]-VIP | 1.9 |
| Ac-[p-F-Phe$^6$,p-NH$_2$-Phe$^{10}$,Lys$^{12}$,Nle$^{17}$,Val$^{26}$,Thr$^{28}$]-VIP | 1.2 |
| Ac-[Glu$^8$,Lys$^{12}$,Nle$^{17}$,Val$^{26}$,Thr$^{28}$,Gly$^{29,30}$,Cys(Acm)$^{31}$]-VIP | 0.45 |
| Ac-[p-NH$_2$-Phe$^{10}$,Lys$^{12}$,Nle$^{17}$,Val$^{26}$,Thr$^{28}$]-VIP | 0.36 |
| Ac-[Glu$^8$,Lys$^{12}$,Nle$^{17}$,Val$^{26}$,Thr$^{28}$,Gly$^{29,30}$,Met$^{31}$]-VIP | 0.25 |

EXAMPLE 84

Bronchodilator Activity of VIP Analogs

The in vivo bronchodilator activity of VIP analogs in guinea pigs was assessed by the tracheal instillation route of administration. This technique utilized male guinea pigs (Hartley strain, Charles River) weighing 400–600 g. Animals were anesthetized with urethane (2 g/kg) intraperitoneally and a polyethylene cannula was inserted into the jugular vein for intravenous drug administration.

The animals were tracheotomized and dosing solutions of distilled water or test compound dissolved in distilled water were administered into the trachea, approximately three-quarter the distance to the carina with a pipette. The concentration of the dosing solution was adjusted to deliver a constant volume of 100 μl. The animals were placed supine for one minute to aid drug delivery to the lung. One minute later, spontaneous breathing was arrested with succinylcholine chloride (1.2 mg/kg) administered intravenously, and the animals were ventilized with a Harvard Model 680 small animal respirator set at 40 breaths/min and 4.0 cm$^3$ stoke volume. The animals were challenged with a maximal constrictory dose of histamine (50 mg/kg, i.v.) and tracheal pressure (cm of water) was recorded from a Statham pressure transducer (P 32 AA).

The change in tracheal pressure was averaged for at least 3 control and 3 drug-treated animals and percent inhibition was calculated. The relative potency of compounds administered by the instillation route was determined by administering various doses of test compound and calculating the median inhibitory dose (ID$_{50}$ value). The ID$_{50}$ was determined from log dose reasons curves generated by at least 3 doses that caused inhibitory effects between 10% and 90%. The correlation coefficient for the regression line of each antagonist was always greater than 0.95.

For determination of the time course of inhibition for various compounds, the time between administration of compound and challenge with histamine was varied. The time course of activity was calculated as the time when inhibition decreased to 40%.

The results summarized in Table II show the in vivo bronchodilator activity of the VIP analogs in comparison to native VIP. These results show that the VIP analogs of the invention possess activity equal to or greater than that of VIP.

TABLE II

Bronchodilator activity of VIP analogs in guinea pigs

| Compound | ED$_{50}$ (nM) |
|---|---|
| Ac-[N-Me-Ala$^1$,Lys$^{12}$,Nle$^{17}$,Val$^{26}$,Thr$^{28}$]-VIP | 8.5 |
| VIP | 7.3 |
| Ac-[p-F-Phe$^6$,p-NH$_2$-Phe$^{10}$,Lys$^{12}$,Nle$^{17}$,Val$^{26}$,Thr$^{28}$]-VIP | 3.0 |
| Ac-[Glu$^8$,Lys$^{12}$,Nle$^{17}$,Val$^{26}$,Thr$^{28}$,Gly$^{29,30}$,Cys(Acm)$^{31}$]-VIP | 2.0 |
| Ac-[p-NH$_2$-Phe$^{10}$,Lys$^{12}$,Nle$^{17}$,Val$^{26}$,Thr$^{28}$]-VIP | 2.0 |
| Ac-[Glu$^8$,Lys$^{12}$,Nle$^{17}$,Val$^{26}$,Thr$^{28}$,Gly$^{29,30}$,Met$^{31}$]-VIP | 1.7 |
| Ac-[p-F-Phe$^6$,Glu$^8$,Lys$^{12}$,Nle$^{17}$,Ala$^{19}$,Val$^{26}$,Thr$^{28}$,Gly$^{29,30}$,Cys(Acm)$^{31}$]-VIP | 0.30 |
| Ac-[Leu$^5$,Orn$^{12}$,Ala$^{17,19}$,Thr$^{25}$,Val$^{26}$,Thr$^{28}$,Gly$^{29,30}$,Cys(Acm)$^{31}$]-VIP | 0.28 |
| Ac-[p-F-Phe$^6$,Lys$^{12}$,Nle$^{17}$,Ala$^{19}$,Val$^{26}$,Thr$^{28}$,Gly$^{29,30}$,Cys(Acm)$^{31}$]-VIP | 0.17 |

I claim:

1. A compound of the formula

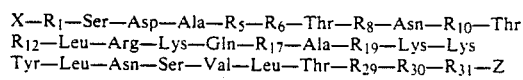

$$X-R_1-Ser-Asp-Ala-R_5-R_6-Thr-R_8-Asn-R_{10}-Thr$$
$$R_{12}-Leu-Arg-Lys-Gln-R_{17}-Ala-R_{19}-Lys-Lys$$
$$Tyr-Leu-Asn-Ser-Val-Leu-Thr-R_{29}-R_{30}-R_{31}-Z$$

wherein

R$_1$ is His or N(CH$_3$) Ala
R$_5$ is Val or Leu
R$_6$ is Phe or P-F-Phe
R$_8$ is Asp or Glu
R$_{10}$ is Tyr or p-NH$_2$-Phe
R$_{12}$ is Lys or Orn
R$_{17}$ Nle or Ala
R$_{19}$ is Val or Ala
R$_{29}$ is Gly or Ala
R$_{30}$ is Gly, Lys or Ala
R$_{31}$ is Gly, Ala, Met, Cys, Cys(Acm), Thr, Ser, or Phe;
Z is —OX$_5$ or —NHX$_5$;
X$_5$ is H or C$_{1-3}$ alkyl;
and X is Acetyl;
and the pharmaceutically acceptable salts thereof.

2. The compound of claim 1 wherein R$_{31}$ is Cys-(Acm).

3. The compound of claim 2 wherein R$_{12}$ is Lys.

4. The compound of claim 3 wherein R$_{17}$ is Nle.

5. The compound of claim 4 wherein R$_{30}$ is Gly.

6. The compound of claim 5 wherein R$_6$ is p-F-Phe and R$_{19}$ is Ala and said compound is Ac-[p-F-Phe$^6$,Lys$^{12}$,Nle$^{17}$,Ala$^{19}$,Val$^{26}$,Thr$^{28}$,Gly$^{29,30}$,Cys(Acm)$^{31}$]-VIP.

7. The compound of claim 5 wherein R$_6$ is p-F-Phe, R$_8$ is Glu, and R$_{19}$ is Ala and said compound is Ac-[p-F-

Phe$^6$,Glu$^8$,Lys$^{12}$,Nle$^{17}$,Ala$^{19}$,Val$^{26}$,Thr$^{28}$,Gly$^{29,30}$,Cys-(Acm)$^{31}$]-VIP.

8. The compound of claim 5 wherein R$_8$ is Glu, and said compound is Ac-[Glu$^8$,Lys$^{12}$,Nle$^{17}$,Val$^{26}$,Thr$^{28}$,-Gly$^{29,30}$,Cys(Acm)$^{31}$]-VIP.

9. The compound of claim 2 wherein R$_5$ is Leu.

10. The compound of claim 9 wherein R$_{12}$ is Orn.

11. The compound of claim 1 wherein R$_{31}$ is Met.

12. The compound of claim 11 wherein R$_{30}$ is Gly.

13. The compound of claim 12 wherein R$_{12}$ is Lys and R$_{17}$ is Nle.

14. The compound of claim 13 wherein R$_8$ is Glu, and said compound is Ac-[Glu$^8$,Lys$^{12}$,Nle$^{17}$,Val$^{26}$,Thr$^{28}$,-Gly$^{29,30}$,Met$^{31}$]-VIP.

15. A pharmaceutical composition comprising an active agent which is a peptide having bronchotracheal smooth muscle relaxant activity and a pharmaceutically acceptable carrier, wherein said peptide has the formula:

```
X—R₁—Ser—Asp—Ala—R₅—R₆—Thr—R₈—Asn—R₁₀—Thr
R₁₂—Leu—Arg—Lys—Gln—R₁₇—Ala—R₁₉—Lys—Lys
Tyr—Leu—Asn—Ser—Val—Leu—Thr—R₂₉—R₃₀—R₃₁—Z
``` wherein
R$_1$ is His or N(CH$_3$)Ala
R$_3$ is Val or Leu
R$_6$ is Phe or p-F-Phe
R$_8$ is Asp or Glu
R$_{10}$ is Tyr or p-NH$_2$-Phe
R$_{12}$ is Lys or Orn
R$_{17}$ Nle or Ala
R$_{19}$ is Val or Ala
R$_{29}$ is Gly or Ala
R$_{30}$ is Gly, Lys or Ala
R$_{31}$ is Gly, Ala, Met, Cys, Cys(Acm), Thr, Ser, or Phe;
Z is -OX$_5$ or -NHX$_5$;
X$_5$ is H or C$_{1-3}$ alkyl;
and X is Acetyl;
and the pharmaceutically acceptable salts thereof.

16. The composition of claim 15 wherein said peptide is selected from the group consisting of:
Ac-[p-F-Phe$^6$,Lys$^{12}$,Nle$^{17}$,Ala$^{19}$,Val$^{26}$,Thr$^{28}$,-Gly$^{29,30}$,Cys(Acm)$^{31}$]-VIP
Ac-[p-F-Phe$^6$,Glu$^8$,Lys$^{12}$,Nle$^{17}$,Ala$^{19}$,Val$^{26}$,Thr$^{28}$,-Gly$^{29,30}$,Cys(Acm)$^{31}$]-VIP
Ac-[N-Me-Ala$^1$,Lys$^{12}$,Nle$^{17}$,Val$^{26}$,Thr$^{28}$]-VIP
Ac-[p-F-Phe$^6$,p-NH$_2$-Phe$^{10}$,Lys$^{12}$,Nle$^{17}$,Val$^{26}$,Thr$^{28}$]-VIP
Ac-[Glu$^8$,Lys$^{12}$,Nle$^{17}$,Val$^{26}$,Thr$^{28}$,Gly$^{29,30}$,Met$^{31}$]-VIP
Ac-[p-NH$_2$-Phe$^{10}$,Lys$^{12}$,Nle$^{17}$,Val$^{26}$,Thr$^{28}$]-VIP
Ac-[Glu$^8$,Lys$^{12}$,Nle$^{17}$,Val$^{26}$,Thr$^{28}$,Gly$^{29,30}$,Cys-(Acm)$^{31}$]-VIP.

* * * * *

UNITED STATES PATENT AND TRADEMARK OFFICE
CERTIFICATE OF CORRECTION

PATENT NO. : 5,141,924

DATED : August 25, 1992

INVENTOR(S) : David Robert Bolin

It is certified that error appears in the above-identified patent and that said Letters Patent is hereby corrected as shown below:

In claim 15, column 45, line 27, replace "$R_3$" with $R_5$

Signed and Sealed this

Nineteenth Day of October, 1993

Attest:

BRUCE LEHMAN

Attesting Officer     Commissioner of Patents and Trademarks